United States Patent
Takano et al.

(10) Patent No.: US 6,184,238 B1
(45) Date of Patent: Feb. 6, 2001

(54) N-HYDROXYUREA DERIVATIVE AND PHARMACEUTICAL COMPOSITION CONTAINING THE SAME

(75) Inventors: Michika Takano; Toshiya Komatsu; Yoshikazu Kawahara, all of Omiya (JP)

(73) Assignee: Nikken Chemicals Co., Ltd., Tokyo (JP)

(*) Notice: Under 35 U.S.C. 154(b), the term of this patent shall be extended for 0 days.

(21) Appl. No.: 09/331,624

(22) PCT Filed: Dec. 25, 1997

(86) PCT No.: PCT/JP97/04856

§ 371 Date: Jun. 23, 1999

§ 102(e) Date: Jun. 23, 1999

(87) PCT Pub. No.: WO98/29408

PCT Pub. Date: Jul. 9, 1998

(30) Foreign Application Priority Data

| Dec. 26, 1996 | (JP) | 8-356359 |
| Dec. 26, 1996 | (JP) | 8-356360 |
| Dec. 26, 1996 | (JP) | 8-356361 |
| Dec. 9, 1997 | (JP) | 9-354016 |
| Dec. 9, 1997 | (JP) | 9-354017 |
| Dec. 9, 1997 | (JP) | 9-354018 |

(51) Int. Cl.$^7$ ............................................ A61K 31/44
(52) U.S. Cl. ........................................ 514/339; 546/277.4
(58) Field of Search ................ 546/277.4; 514/339

(56) References Cited

U.S. PATENT DOCUMENTS

| 3,468,894 | 9/1969 | Pfenninger | 260/294.8 |
| 5,095,031 | 3/1992 | Brooks et al. | 514/419 |
| 5,132,319 | * 7/1992 | Girard et al. | |
| 5,459,150 | 10/1995 | Brooks | 2/428 |

FOREIGN PATENT DOCUMENTS

| 544819 | 6/1993 | (EP) . |
| 643059 | 3/1995 | (EP) . |
| 59-225181 | 12/1984 | (JP) . |
| 6 9571 | 1/1991 | (JP) . |
| 5-78321 | 3/1993 | (JP) . |
| 5-178855 | 7/1993 | (JP) . |
| WO 97/10206 | 3/1907 | (WO) . |
| WO 92/01682 | 2/1992 | (WO) . |
| WO 92/03132 | 3/1992 | (WO) . |
| WO 95/12589 | 5/1995 | (WO) . |
| WO 96/23772 | 8/1996 | (WO) . |

OTHER PUBLICATIONS

H.R. Snyder et al, Boron Fluoride as a Condensing Agent in the Fischer Indole Synthesis, Journal of the American Chemical Society, vol. 65, pp. 2452–2454.

Richard F. Borch et al, The Cyanohydridoborate Anion as a Selective Reducing Agent, Journal of the American Chemical Society, Jun. 1971, pp. 2897–2904.

Yee–Sheng Kao et al, "3–Methyl– and 3–Ethyl–2–2'–pyridylindole", Journal of the Chemical Society, 1955, pp. 2865–2870.

* cited by examiner

Primary Examiner—John Kight
Assistant Examiner—Binta Robinson
(74) Attorney, Agent, or Firm—Christie, Parker & Hale, LLP

(57) ABSTRACT

An N-hydroxyurea derivative having an antiallergic action or anti-inflammatory action having the formula

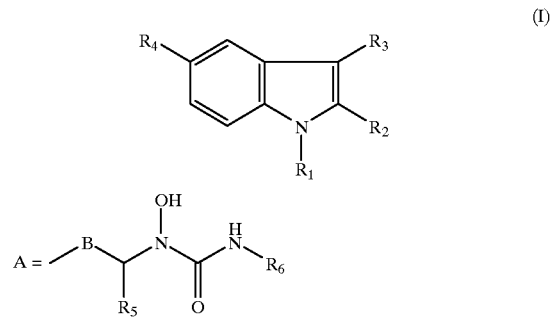

wherein, either one of $R_1$, $R_3$, and $R_4$ represents A, either one of the other groups of $R_1$, $R_3$, and $R_4$ and $R_2$ represents a 3-pyridyl group or 3-pyridylalkyl group, the remaining groups of $R_1$, $R_2$, $R_3$, and $R_4$ independently represent a hydrogen atom, halogen atom, or a substituted or unsubstituted $C_1$ to $C_8$ alkyl group, $R_5$ represents a hydrogen atom or lower alkyl group, $R_6$ represents a hydrogen atom, lower alkyl group, $C_3$ to $C_7$ cycloalkyl group, or a substituted or unsubstituted phenyl group, where the substituent represents a halogen atom, lower alkyl group, or lower alkoxy group, B represents a bond, $C_1$ to $C_{20}$ alkylene group, $C_2$ to $C_8$ alkenylene group, or $C_2$ to $C_8$ alkynylene group or B—C($R_5$) represents a $C_2$ to $C_6$ alkylene group having a benzene ring in the middle thereof or its pharmacologically acceptable salt or the hydrate or solvate thereof.

16 Claims, No Drawings

N-HYDROXYUREA DERIVATIVE AND PHARMACEUTICAL COMPOSITION CONTAINING THE SAME

CROSS-REFERENCE TO RELATED APPLICATIONS

This application is prepared under 35 U.S.C. Section 371 of International Patent Application PCT/JP97/04856, filed Dec. 25, 1997.

TECHNICAL FIELD

The present invention relates to novel N-hydroxyurea derivative and pharmaceutical composition containing the same. These compounds have a lipoxygenase inhibitory activity and a thromboxane synthase inhibitory activity, so are useful in treating or alleviating allergic diseases or inflammatory diseases.

BACKGROUND ART

In recent years, the role of chemical mediators in asthma and other allergic diseases has been quickly elucidated. In addition to histamine, PAF, leukotrienes, thromboxane $A_2$, etc. have become known. It has been shown that leukotrienes are biosynthesized by the action of 5-ipoxygenase from arachidonic acid, and thromboxane $A_2$ is biosynthesized by thromboxane synthase after the catabolism with cyclooxygenase from arachidonic acid. Further, leukotrienes and thromboxane $A_2$ have both been found to be important chemical mediators in allergic reactions causing various diseases such as asthma, psoriasis, enteritis, nephritis, ulcers, and ischemia. Therefore, if it were possible to inhibit the biosynthesis of both chemical mediators, a greater effect could be obtained in treating or alleviating the above diseases when compared with the inhibition of single mediator.

Recently, as compounds for inhibiting the biosynthesis of such two mediators, benzothiazole derivatives (Japanese Unexamined Patent Publication (Kokai) No. 5-178855), quinone derivatives (Japanese Unexamined Patent Publication (Kokai) No. 5-78321), imidazolylphenol derivatives (Japanese Unexamined Patent Publication (Kokai) No. 6-9571), and N-hydroxyurea derivatives (WO96/23772) have become known.

DISCLOSURE OF THE INVENTION

The object of the present invention is to provide compounds capable of inhibiting both the biosynthesis of leukotrienes and thromboxane $A_2$, that is, novel compounds having both the dual inhibition against lipoxygenase and thromboxane synthase at the same time.

In accordance with the present invention, there are provided N-hydroxyurea derivatives having the formula (I):

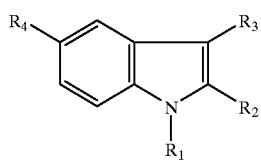

(I)

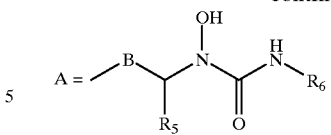

-continued wherein, either one of $R_1$, $R_3$ and $R_4$ represents A, either one of the other groups of $R_1$, $R_3$, and $R_4$ and $R_2$ represents a 3-pyridyl group or 3-pyridyl alkyl group, the remaining groups of $R_1$, $R_2$, $R_3$, and $R_4$ independently represent a hydrogen atom, halogen atom, or a substituted or unsubstituted $C_1$ to $C_8$ alkyl group where the substituent represents a halogen atom, cyano group, phenyl group, carboxyl group, or lower alkoxycarbonyl group, $R_5$ represents a hydrogen atom or lower alkyl group, $R_6$ represents a hydrogen atom, lower alkyl group, $C_3$ to $C_7$ cycloalkyl group, or a substituted or unsubstituted phenyl group, where the substituent represents a halogen atom, lower alkyl group, or lower alkoxy group, B indicates a bond, $C_1$ to $C_{20}$ alkylene group, $C_2$ to $C_8$ alkenylene group, or $C_2$ to $C_8$ alkynylene group or B—$C(R_5)$ represents a $C_2$ to $C_6$ alkylene group having a benzene ring in the middle thereof.

In accordance with the present invention, there is further provided a pharmaceutical composition comprising this N-hydroxyurea derivative or its optically active substances, pharmaceutically acceptable salts, or the hydrates or solvates thereof as an active principle, in particular an anti-asthmatic or anti-inflammatory drug.

BEST MODE FOR CARRYING OUT THE INVENTION

The present invention will now be explained in further detail.

The present invention is as explained above, but as preferable compounds, N-hydroxyurea derivatives wherein, in the formula (I), either one of $R_1$, $R_3$, and $R_4$ represents A, either one of the other groups of $R_1$, $R_3$, and $R_4$ and $R_2$ represents a 3-pyridyl group or 3-pyridyl lower alkyl group, especially a 3-pyridyl group or 3-pyridylmethyl group, the remaining groups of $R_1$, $R_2$, $R_3$, and $R_4$ independently represent a hydrogen atom, halogen atom, or a substituted or unsubstituted $C_1$ to $C_5$ alkyl group where the substituent represents a carboxyl group, methoxycarbonyl group, or ethoxycarbonyl group etc., $R_5$ represents a hydrogen atom, methyl group, or ethyl group, $R_6$ represents a hydrogen atom, methyl group, ethyl group, or $C_3$ to $C_6$ cycloalkyl group, B represents a bond, $C_1$ to $C_{12}$ alkylene group, $C_2$ to $C_5$ alkenylene group, or $C_2$ to $C_5$ alkynylene group, or B—$C(R_5)$ represents a $C_2$ to $C_4$ alkylene group having a benzene ring in the middle thereof may be mentioned.

Further, in the present invention, as preferable compounds in the case where $R_1$ is A, N-hydroxyurea derivatives where either one of $R_2$, $R_3$, and $R_4$ represents a 3-pyridyl group or 3-pyridylmethyl group, the other groups of $R_2$, $R_3$, and $R_4$ preferably represent a hydrogen atom, halogen atom, or a substituted or unsubstituted $C_1$ to $C_5$ alkyl group where the substituent represents a carboxyl group, methoxycarbonyl group, or ethoxycarbonyl group, especially a hydrogen atom, chlorine atom, fluorine atom, methyl group, carboxyalkyl group such as a carboxypentyl group, or lower alkoxycarbonylalkyl group such as an ethoxycarbonylbutyl group, $R_5$ preferably represents a hydrogen atom or lower alkyl group such as a methyl group or ethyl group, especially a hydrogen atom or methyl group, $R_6$ preferably represents a hydrogen atom, or lower alkyl group such as a methyl group or ethyl group, or $C_3$ to $C_6$ cycloalkyl group, especially a hydrogen atom or cyclohexyl group, B preferably represents a $C_1$ to $C_{15}$ alkylene group or $C_2$ to $C_8$ alkenylene group, more preferably a $C_1$ to $C_{12}$ alkylene group, particularly preferably a $C_1$ to $C_6$ linear alkylene group may be mentioned.

As preferable compounds in the case where $R_3$ is A, N-hydroxyurea derivatives where, in the formula (I), either one of $R_1$, $R_2$, and $R_4$ represents a 3-pyridyl group, 3-pyridylmethyl group, or 3-pyridylpropyl group, the other groups of $R_1$, $R_2$, and $R_4$ each preferably represents a hydrogen atom, halogen atom, or $C_1$ to $C_5$ alkyl group, especially a hydrogen atom, halogen atom, or methyl group, $R_5$ preferably represents a hydrogen atom or lower alkyl group such as a methyl group or ethyl group, especially a hydrogen atom or methyl group, $R_6$ preferably represents a hydrogen atom, lower alkyl group such as a methyl group or ethyl group, or $C_3$ to $C_6$ cycloalkyl group, especially a hydrogen atom, B preferably represents a bond, $C_1$ to $C_5$ alkylene group, $C_2$ to $C_5$ alkenylene group, especially a bond or vinylene group, or B—$C(R_5)$ represents a $C_1$ to $C_4$ alkylene group having a benzene ring in the middle thereof may be mentioned.

As preferable compounds in the case where $R_4$ is A, N-hydroxyurea derivatives where, in the formula (I), either one of $R_1$, $R_2$, and $R_3$ represents a 3-pyridyl group, 3-pyridylmethyl group, or 3-pyridylpropyl group, the other groups of $R_1$, $R_2$, and $R_3$ each preferably represents a hydrogen atom, halogen atom, or a substituted or unsubstituted $C_1$ to $C_5$ alkyl group where the substituent represents a carboxyl group, methoxycarbonyl group, or ethoxycarbonyl group, especially a hydrogen atom, methyl group, carboxybutyl group, or ethoxycarbonylbutyl group, $R_5$ preferably represents a hydrogen atom or lower alkyl group such as a methyl group or ethyl group, especially a hydrogen atom or methyl group, $R_6$ preferably represents a hydrogen atom, lower alkyl group such as a methyl group or ethyl group, or $C_3$ to $C_6$ cycloalkyl group, especially a hydrogen atom, B preferably represents a bond, $C_1$ to $C_8$ alkylene group, $C_2$ to $C_5$ alkenylene group, or $C_2$ to $C_5$ alkynylene group, especially a bond, ethylene group, vinylene group, or ethynylene group may be mentioned.

Further, in the present invention, the N-hydroxyurea derivatives represented by the formula (I) may be pharmacologically acceptable salts, specifically an inorganic acid salt formed from hydrochloric acid, hydrobromic acid, sulfuric acid, bisulfuric acid, or phosphoric acid or an organic acid salt formed from formic acid, acetic acid, citric acid, fumaric acid, gluconic acid, lactic acid, maleic acid, succinic acid, tartaric acid, methanesulfonic acid, benzenesulfonic acid, toluenesulfonic acid, etc. may be mentioned.

Specific examples of preferable compounds of the present invention are shown below.

N-hydroxy-N-[12-[1-[2-(3-pyridyl)indolyl]]dodecyl]urea (Compound 1)

N-hydroxy-N-[10-[1-[2-(3-pyridyl)indolyl]]decyl]urea (Compound 11)

N-hydroxy-N-[2-[1-[3-(3-pyridyl)indolyl]]ethyl]urea (Compound 19)

N-hydroxy-N-[2-[1-[2-methyl-3-(3-pyridyl) indolyl]] ethyl]urea (Compound 20)

N-hydroxy-N-[6-[1-[3-(3-pyridyl)indolyl]]hexyl]urea (Compound 21)

N-hydroxy-N-[6-[1-[5-fluoro-3-(3-pyridylmethyl) indolyl]]hexyl]urea (Compound 22)

N-hydroxy-N-[3-[1-(3-pyridylmethyl)indolyl]methyl] urea (Compound 26)

N-hydroxy-N-[3-[1-[3-(3-pyridyl)propyl]indolyl]methyl] urea (Compound 28)

N-hydroxy-N-[3-[5-bromo-1-(3-pyridylmethyl) indolyl] methyl]urea (Compound 29)

N-hydroxy-N-[3-[2-methyl-i-(3-pyridylmethyl) indolyl] methyl]urea (Compound 30)

N-hydroxy-N-[1-[3-[1-(3-pyridylmethyl) indolyl]]ethyl] urea (Compound 31)

N-hydroxy-N-[3-[5-fluoro-1-(3-pyridylmethyl) indolyl] methyl]urea (Compound 32)

N-hydroxy-N-[5-[1-(3-pyridylmethyl)indolyl]methyl] urea (Compound 33)

Ethyl 5-[1-[5-(N-hydroxyureidomethyl)-3-methyl-2-(3-pyridyl)indolyl]]pentanoate (Compound 36)

N-hydroxy-N-[5-[1-methyl-3-(3-pyridyl)indolyl]methyl] urea (Compound 40)

N-[1-[5-[1,3-dimethyl-2-(3-pyridyl)indolyl]ethyl]]-N-hydroxyurea (Compound 41)

N-hydroxy-N-[1-[5-[1-(3-pyridylmethyl) indolyl]]ethyl] urea (Compound 42)

N-[3-[5-[1,3-dimethyl-2-(3-pyridyl)indolyl]]-2-propinyl]-N-hydroxyurea (Compound 43)

N-hydroxy-N-[1-[5-(1-methyl-3-(3-pyridyl) indolyl]] ethyl]urea (Compound 45)

N-hydroxy-N-[1-[5-[1-methyl-3-(3-pyridyl) indolyl]] ethyl]urea (Compound 46)

The N-hydroxyurea derivatives provided by the present invention may be produced by many methods. The usable starting substances are commercially available compounds or compounds produced from known compounds by known methods.

That is, the compound according to the present invention represented by the formula (I) may be synthesized, for example, by the following reaction process (1) and further may be synthesized by methods other than this reaction process.

Synthetic method 1

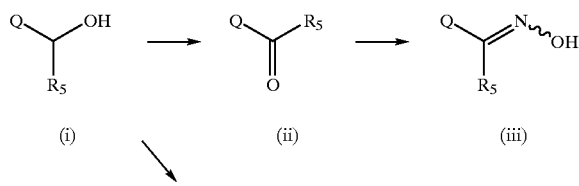

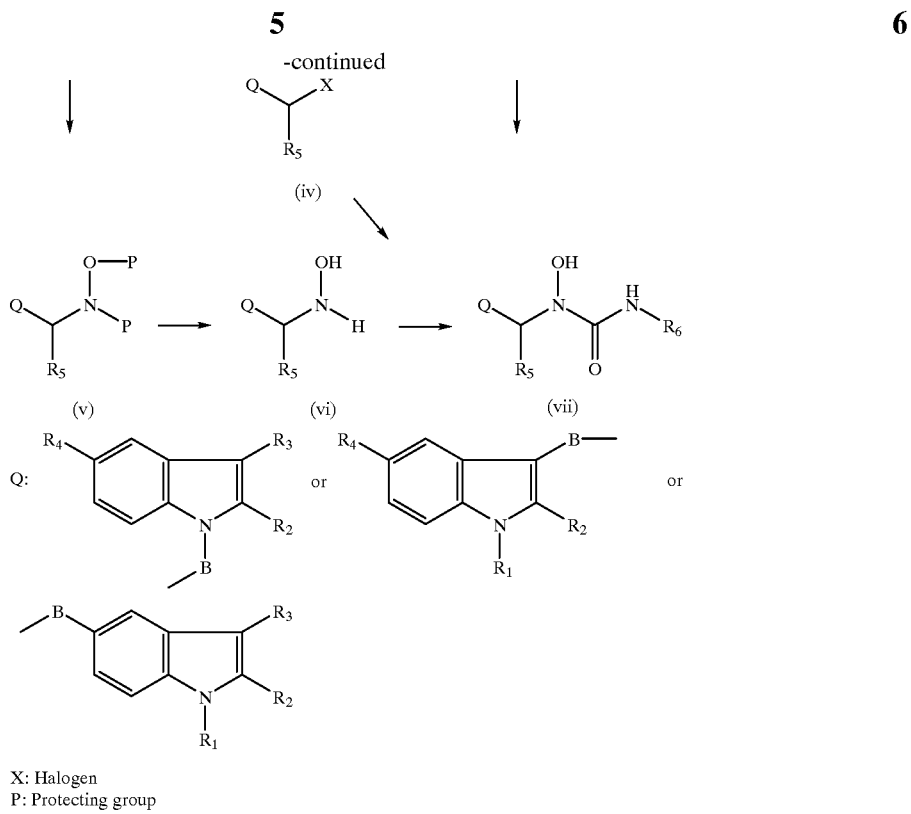

X: Halogen
P: Protecting group wherein, $R_1$, $R_2$, $R_3$, $R_4$, $R_5$, $R_6$, and B are the same as those defined in the formula (I).

The reactions used in this synthetic process are known, standard methods. That is, hydroxyamine (vi) and trimethylsilyl isocyanate are reacted to obtain the target compound (vii). Further, in the compounds represented by the formula (I), for example, a compound where $R_6$ is a methyl group, cyclohexyl group, etc. may be synthesized by the reaction of the hydroxylamine and the corresponding $R_6$—NCO (e.g., methyl isocyanate, cyclohexyl isocyanate).

Further, as the other method, a compound where $R_6$ is a hydrogen atom may be easily synthesized from hydroxylamine (vi) using a known standard method. For example, hydroxylamine may be reacted under an acidic condition with potassium cyanate or sodium cyanate to prepare the hydroxyurea (see WO95/12589).

Hydroxylamine (vi) is easily synthesized from a ketone or aldehyde (ii) or alcohol (i) or halogen compound (iv) using a known standard method. For example, it is possible to react a corresponding alcohol (i) using a condition of Mitsunobu reaction with N,O-bis(tert-butoxycarbonyl) hydroxylamine to synthesize an N,O-protected hydroxylamine (vi), followed by an acid hydrolysis to give the hydroxylamine (vi) (see WO92/01682).

As the other method, hydroxylamine (vi) may be synthesized by a reaction between a carbonyl compound (ii), that is, a ketone or aldehyde etc., and hydroxylamine hydrochloride to synthesize an oxime (iii), followed by reducing with a suitable reducing agent (see *Journal of American Chemical Society*, 1971, vol. 93, p. 2897). As the reductant, sodium cyanoborohydride, borane-pyridine complex, borane-triethylamine complex, borane-dimethylsulfide complex etc. may be mentioned. As the preferable agents sodium cyanoborohydride, a borane-pyridine complex, etc. may be mentioned.

Further, as the other method, hydroxylamine (vi) is easily synthesized from a reaction intermediate, halogen compound (iv) using a known standard method. For example, a corresponding halogen compound is reacted in N-methyl-2-pyrrolidinone with a 50% aqueous hydroxylamine solution to obtain hydroxylamine (vi) (see WO97/10,206).

Further, the synthetic intermediate aldehyde, ketone, or other carbonyl compound (ii) is synthesized by a standard method. For example, it is synthesized by oxidation of alcohol (i). The oxidation reaction used may be manganese dioxide oxidation, Jones' oxidation, Swern oxidation, etc.

On the other hand, the synthetic intermediate alcohol (i) is also synthesized by a standard method. For example, a carbonyl compound (ii), such as an aldehyde, ketone and ester, is reduced by various reductant. As the reductant used here, sodium borohydride, lithium aluminum hydride, diisobutylaluminum hydride, etc. may be mentioned.

Further, the alcohol (i) may be synthesized, as another method, by using for a Grignard reagent or organometallic compound etc. from the carbonyl compound. As a preferable reaction reagent, methylmagnesium bromide may be mentioned. Further, the reaction is performed in a range of from $-78°$ C. to room temperature, but in this case $0°$ C. is preferable.

The synthetic intermediate halogen compound (iv) is synthesized by halogenation of the alcohol (i) by a standard method. For example, it is synthesized by reacting a suitable alcohol with carbon tetrahalide and triphenyl phosphine in methylene chloride.

The indole compounds used in the present invention may be synthesized from a readily available other indole compound by a standard method. For example, a suitable indole compound may lead to a formylindole compound by a Vilsmeier reagent, or an indole compound may lead to an acylindole compound by an acid chloride or acid anhydride by a Friedel Crafts reaction. As a preferable process, condensation under Vilsmeier-Haack reaction conditions of, for example, dimethylformamide in the presence of phosphorus oxychloride may be mentioned.

The precursor of a compound where B in the formula (I) is a vinylene group or ethylene group is increased number of carbon atom by using a Wittig reaction, Horner-Emmons reaction, etc. on those having aldehyde. As the phosphonium salt and phosphonate ester used here, trimethylphosphonoacetate, ethyl(triphenyl phosphoranylidene)acetate or ethyl diethylphosphono acetate etc. may be mentioned. Further, according to the Horner-Emmons reaction, synthesis is carried out by reacting with phosphonocarboanion which is formed by treating alkyl phosphorate diester with a base. The base used here may be sodium hydride, sodium amide, etc.

Further, the double bond of the olefin is reduced by a known method (e.g. catalytic hydrogenation). The catalyst used here may be platinum oxide, platinum on activated carbon, palladium on activated carbon, Raney nickel, etc. As a preferable example, palladium on activated carbon may be mentioned. The reaction may be performed in the range of from atmospheric pressure to 5 atmospheres.

Further, the intermediate alcohol of the compound where B in the formula (I) has a triple bond is easily synthesized by a known method using a catalyst. For example, reactions using various palladium catalysts can be mentioned. As a preferable reaction, a method of reacting a suitable halogen, 10% palladium on carbon, triphenyl phosphine, copper iodide and potassium carbonate, in mixed solvent of 1,2-dimethoxyethane and water solvent may be mentioned to corresponding alcohol (see Synlett 1995, p. 1115).

In the present invention, among the compounds having the formula (II):

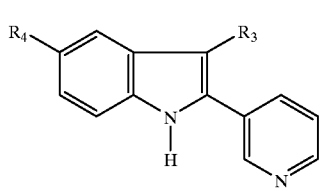

(II)

wherein, $R_3$ and $R_4$ are as defined in the formula (I), a compound where $R_3$ is a halogen atom is synthesized, for example, from a compound where $R_3$ is a hydrogen atom, by a standard method, for example, a reaction with an N-halosuccinimide.

Further, the starting material of the indole compound having the formula (II) is described in the references (see U.S. Pat. No. 3, 468, 894, *Journal of the Chemical Society*, 1955, p. 2865) or produced in the same way as the known Fischers method for synthesis of indole in the presence of a condensing agent, for example, ethanolic hydrogen chloride or polyphosphoric acid, from the suitable substituted phenyl hydrazine and a ketone having the formula:3-PyCOCH$_2$R$_3$ (see "Heterocyclic Compounds—Indoles Part I", edited by Freehan pp. 232 to 317, *Journal of the American Chemical Society*, 1943, vol. 65, pp. 2452 to 2454).

Further, among the intermediates having the formula (III):

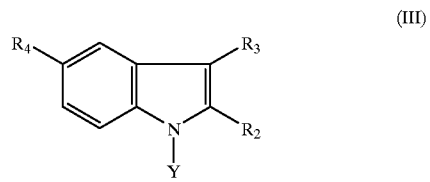

(III)

wherein, $R_2$, $R_3$, and $R_4$ are as defined in formula (I), Y represents a hydrogen atom, methyl group, 3-pyridyl lower alkyl group, alkoxycarbonyl $C_1$ to $C_{20}$ alkyl group, carboxy $C_1$ to $C_{20}$ alkyl group, 4-carboxybenzyl group, N-hydroxyaminoalkyl group which may have a protective group, or hydroxy $C_1$ to $C_{20}$ alkyl group which may have a protective group, an indole compound where Y represents a methyl group, 3-pyridyl lower alkyl group, butyl group substituted with a $C_1$ to $C_4$ alkoxycarbonyl group or 4-carboxybutyl group is synthesized from an indole compound where Y is a hydrogen atom. For example, an indole compound where Y is a hydrogen atom is synthesized by treatment in an inert solvent (e.g., dimethylformamide, tetrahydrofuran) with a strong base (e.g., sodium hydride), followed by reacting with a corresponding alkylating agent (e.g., alkyl halide, lower alkoxyalkyl halide, hydroxyalkyl halide, N-hydroxyaminoalkyl halide). The protective group, for example, for a hydroxy $C_1$ to $C_{20}$ alkyl halide, tert-butyldiphenylsilyl, tert-butyldimethylsilyl, methoxymethyl, and tetrahydropyranyl etc. may be mentioned and for N-hydroxyaminoalkylhalide, tert-butoxycarbonyl etc. may be mentioned. The reaction is accelerated by a crown ether such as 15-crown-5 or 4-dimethylaminopyridine etc.

Further, the starting material for the indole compound having the formula (IV):

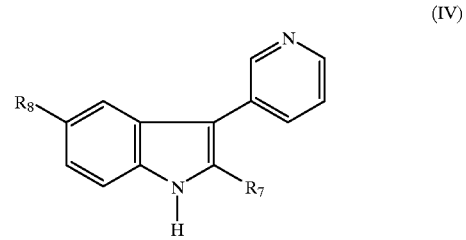

(IV)

wherein, $R_7$ and $R_8$ represent a hydrogen atom, halogen atom, or methyl group is described in the reference (e.g., European Patent No. 643059). And these compounds are synthesized in the presence of a condensing agent such as concentrated hydrochloric acid from the suitable substituted phenylhydrazine and that suitable pyridine derivative by the method described in the above reference.

Further, among the intermediates having the following formula (V):

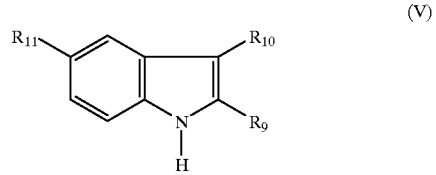

(V)

wherein, $R_9$ represents a hydrogen atom or methyl group, $R_{10}$ represents a hydrogen atom, 3-pyridylmethyl group, or 4-carboxybenzyl group, and $R_{11}$ represents a hydrogen atom, halogen atom, or methyl group. An indole compound where $R_{10}$ is a 3-pyridylmethyl group or 4-carboxybenzyl group is synthesized from an indole compound where $R_{10}$ is a hydrogen atom by a standard method (see Japanese Unexamined Patent Publication (Kokai) No. 59-225181). For example, an indole compound, in the formula (III), $R_{10}$ is a hydrogen atom is reacted with a Grignard reagent or an organometallic compound, preferably methylmagnesium bromide, followed by reaction with a alkyl halide in an inert solvent (e.g., dimethylformamide, tetrahydrofuran) to synthesize an indole compound where $R_{10}$ is a 3-pyridylmethyl group, is reacted with 4-cyanobenzylbromide, followed by dropwise adding a dilute acid (e.g., 10% hydrochloric acid) to synthesize an indole compound where $R_{10}$ is a 4-carboxybenzyl group.

The compounds obtained by the above reactions may be isolated and purified by known methods such as recrystallization or silica gel column chromatography.

Among the compounds of the present invention, some have asymmetric carbons, therefore optically active forms can also exist. Therefore, the compounds of the present invention can exist as separate (+) and (−) optically active forms and racemates or (±) mixtures. Further, optically active forms can be obtained by organic chemical methods well known for that purpose.

The compounds of the present invention may be administered by a suitable method of administration such as oral or nonoral administration when used as a drug for the treatment of allergic diseases or inflammatory diseases. As a form of oral administration, for example, tablets, granules, capsules, pills, powders, liquids, etc. may be exemplified and, further, as a form of nonoral administration, injections, inhalants, suppositories, liquids, etc. may be exemplified. When preparing these medically administered compounds, the compound of the present invention or its salt may be prepared according to an ordinary method.

For example, in the case of oral administration, the preparations can be prepared into the desired form using excipients such as lactose, glucose, corn starch, sucrose, a disintegrator such as calcium carboxymethylcellulose, hydroxypropylcellulose; a lubricant such as calcium stearate, magnesium stearate, talc, polyethylene glycol, hardened oil, a binder such as hydroxypropylcellulose, hydroxypropylmethyl-cellulose, carboxymethylcellulose, polyvinyl alcohol, gelatin, arabia gum, a humectant such as glycerin, ethylene glycol; and, in addition, surfactants, taste adjusters, etc., if necessary.

Further, in the case of a non-oral drug, a diluent such as water, ethanol, glycerin, propylene glycol, polyethylene glycol, agar, tragacanth gum may be used and solution adjuvants, buffer agents, preservatives, flavors, coloring agents, etc. may be optionally used.

When formulating the compounds of the present invention as drugs for the treatment of allergic diseases or inflammatory diseases, the dosage, as the compound of the present invention, is per adult, in the case of oral administration, 5 to 1000 mg per day, preferably 5 to 100 mg, and in the case of non-oral administration, 1 to 200 mg per day, preferably 1 to 20 mg. The desired effect of treatment can be expected by administration divided into one to three dosages per day.

EXAMPLES

The present invention will now be explained below by Examples, but the present invention is of course not limited to these Examples:

Example 1

N-Hydroxy-N-[12-[1-[2-(3-pyridyl) indolyl]]dodecyl] urea (Compound 1)

(1) Synthesis of N,O-bis(tert-butoxycarbonyl)-12-[1-[2-(3-pyridyl)indoly]idodecy]hydroxylamine Under argon, a dimethylformamide (15 ml) solution of 2-(3-pyridyl)indole (1.5 g) was added dropwise to dimethylformamide (10 ml) in which 60% sodium hydride (371 mg) was suspended, followed by stirring at room temperature for 30 minutes. At 0° C., the mixture was added dropwise to, a dimethyl-formamide (10 ml) solution of 12-N,O-bis-(tert-butoxycarbonyl)aminododecyl bromide (4.45 g) followed by stirring at room temperature for 2.5 hours. After the reaction, a saturated aqueous sodium hydrogencarbonate solution was added at 0° C., and the mixture was extracted with ethyl acetate. The organic phase was washed with brine, dried over magnesium sulfate, then the solvent was evaporated in vacuo and the residue was purified by silica gel column chromatography to obtain N,O-bis-(tert-butoxycarbonyl)-12-[1-[2-(3-pyridyl)indolyl] dodecy]hydroxylamine (2.72 g).

The starting material 2-(3-pyridyl)indole was synthesized by the method described in U.S. Pat. No. 3,468,894.

Further, 12-N,O-bis-(tert-butoxycarbonyl) aminododecyl bromide was produced in the following way. Under argon, triphenylphosphine (6.43 g) and N,O-bis-tert-butoxycarbonylhydroxylamine (5.72 g) were added at −10° C. to tetrahydrofuran (100 ml) solution of 12-bromododecyl alcohol (5 g), then diethyl azocarboxylate (4.41 ml) was added and the mixture was stirred for 5.5 hours at the same temperature. After the reaction, the solvent was evaporated in vacuo and the residue was purified by silica gel column chromatography to obtain 12-N,O-bis-(tert-butoxycarbonyl) aminododecyl bromide (2.72 g).

(2) Synthesis of 12-[1-[2-(3-pyridyl) indolyl]] dodecylhydroxylamine

Trifluoroacetic acid (15 ml) was added dropwise to a dichloromethane (15 ml) solution of the product obtained from (1) (2.72 g) and the mixture stirred at room temperature for 20 minutes. After the reaction, saturated aqueous sodium hydrogencarbonate solution was added and the mixture extracted with ethyl acetate. The organic phase was washed with brine and was dried over magnesium sulfate, the solvent was evaporated in vacuo, and the residue was purified by silica gel column chromatography to obtain 12-[1-[2-(3-pyridyl)indolyl]dodecy]hydroxylamine (1.64 g).

(3) Synthesis of N-hydroxy-N-[12-[1-[2-(3-pyridyl) indolyl]dodecyl]urea

Under argon, trimethylsilyl isocyanate (608 μl) was added to tetrahydrofuran (10 ml) solution of the product obtained in (2) (1.64 g) and the mixture was stirred at room temperature for 23 hours. After the reaction, water was added and the mixture was stirred for 20 minutes, then the solvent was evaporated in vacuo and the residue was purified by silica gel column chromatography to obtain N-hydroxy-N-[12-[1-[2-(3-pyridyl)indolyl]dodecyl]urea (1.34 g).

$^1$H-NMR (DMSO-d$_6$): δ1.03–1.20 (m, 16H), 1.46 (m, 4H), 3.29 (m, 2H), 4.19 (m, 2H), 6.22 (s, 2H), 6.62 (s, 1H), 7.07 (m, 1H), 7.19 (m, 1H), 7.53 (m, 2H), 7.58 (d, 1H), 7.97 (m, 1H), 8.63 (m, 1H), 8.75 (d, 1H), 9.17 (s, 1H)

Example 2

N-Hydroxy-N-[6-[1-[2-(3-pyridyl)indolyl]]hexyl]urea (Compound 2)

(1) Synthesis of 1-(6-Tert-butyldiphenylsilyloxyhexyl)-2-(3-pyridyl)indole 6-(Tert-butyldiphenylsilyloxy)hexylbromide instead of 12-N,O-bis-(tert-butoxycarbonyl)aminododecylbromide in Example 1(1), was used for the same way to obtain 1-[6-(tert-butyldiphenylsilyloxy)hexyl]-2-(3-pyridyl)indole. The starting material, 6-(tert-butyldiphenylsilyl) oxyhexylbromide was synthesized in the following way. Under argon 6-bromohexyl alcohol (5.36 g) and tert-butyldiphenylchlorosilane (10.25 g) were stirred in the presence of imidazole (3.45 g) in dimethylformamide (15 ml) at room temperature for 17.5 hours. After the reaction, water was added at 0° C. and the mixture was extracted with ethyl acetate. The extract was washed with brine, then dried over magnesium sulfate, then the solvent was evaporated in vacuo and the residue was purified by silica gel column chromatography to obtain 6-(tert-butyldiphenylsilyloxy) hexylbromide (10.45 g).

(2) Synthesis of 6-[1-[2-(3-pyridyl) indolyl]]hexanol

The product obtained in (1) (1.77 g) was stirred in tetrahydrofuran (20 ml) in the presence of tetra-n-butylammonium fluoride hydrate (1.57 g) at room temperature for 3 hours. After the reaction, saturated aqueous sodium hydrogencarbonate solution was added and the mixture was extracted with ethyl acetate. The organic phase was washed with brine and dried over magnesium sulfate, then the solvent was evaporated in vacuo and the residue was purified by silica gel column chromatography to obtain 6-[1-[2-(3-pyridyl)indolyl]]hexanol (935 mg).

(3) Synthesis of N,O-bis(tert-butoxycarbonyl)-6-[1-[2-(3-pyridyl)indolyl]]hexylhydroxylamine Under argon, triphenylphosphine (1.10 g) and N,O-bis-tert-butoxycarbonylhydroxylamine (980 mg) were added to a tetrahydrofuran (15 ml) solution of the product obtained in (2) (930 mg) at −10° C., then diethyl azocarboxylate (716 ml) was added, and stirred at the same temperature for 2.5 hours. After the reaction, the solvent was evaporated in vacuo and the residue was purified by silica gel column chromatography to obtain N,O-bis(tert-butoxycarbonyl)-6-[1-[2-(3-pyridyl)indolyl]]hexylhydroxylamine (1.58 g).

(4) Synthesis of N-hydroxy-N-[6-[1-[2-(3-pyridyl) indolyl]]hexyl]urea

The product obtained in (3) (1.58 g) was treated in the same way as in Example 1 (2) to (3) to obtain N-hydroxy-N-[6-[1-[2-(3-pyridyl)indolyl]]hexyl]urea (833 mg).

$^1$H-NMR (DMSO-d$_6$): δ1.08 (m, 4H), 1.33 (m, 2H), 1.55 (m, 2H), 3.19 (m, 2H), 4.19 (m, 2H), 6.16 (s, 2H), 6.63 (s, 1H), 7.07 (d, 1H), 7.20 (d, 1H), 7.56 (m, 1H), 8.65 (m, 1H), 8.76 (d, 1H), 9.10 (s, 1H)

Example 3

N-Hydroxy-N-[2-[1-[2-(3-pyridyl)indolyl]]ethyl]urea (Compound 3)

(1) Synthesis of ethyl 1-[2-(3-pyridyl)indolyl]acetate

Ethyl 2-bromoacetate instead of 12-N,O-bis-(tert-butoxycarbonyl)aminododecylbromide of Example 1(1), was used for the same manner to obtain ethyl 1-[2-(3-pyridyl)indolyl]acetate.

(2) Synthesis of 2-[1-[2-(3-pyridyl) indolyl]]ethanol

Under argon, lithium aluminum hydride (1.73g) was added to tetrahydrofuran (120 ml) solution of the product obtained in (1) (4.67 g) at 0° C., and the mixture stirred at 0° C. for 15 minutes. After the reaction, water (3.3 ml), 15% aqueous sodium hydroxide solution (3.3 ml), and water (9.9 ml) were added at 0° C., and stirred at room temperature for 15 minutes. Magnesium sulfate was added, and the mixture was stirred for a one hour, then the insoluble matters were filtered out and the solvent was evaporated in vacuo. The residue was purified by silica gel column chromatography to obtain 2-[1-[2-(3-pyridyl) indolyl]]ethanol(3.01 g).

(3) Synthesis of N-hydroxy-N-[2-[1-[2-(3-pyridyl) indolyl]]ethyl]urea

The product obtained in (2)(3.31 g) was treated in the same way as in Example 2 (3) to (4) to obtain N-hydroxy-N-[2-[1-[2-(3-pyridyl)indolyl]]ethyl]urea (488 mg).

$^1$H-NMR (DMSO-d$_6$): δ3.61 (m, 2H), 4.30 (m, 2H), 6.35 (s, 2H), 6.65 (s, 1H), 7.10 (m, 1H), 7.23 (m, 1H), 7.53 (m, 2H), 7.58 (m, 1H), 8.01 (m, 1H), 8.64 (m, 1H), 8.78 (d, 1H), 9.47 (s, 1H)

Example 4

N-[6-[1-[3-Chloro-2-(3-pyridyl)indolyl]]hexyl]-N-hydroxyurea (Compound 4)

(1) Synthesis of 6-[1-[3-chloro-2-(3-pyridyl) indolyl]] hexanal

Under argon, dimethylsulfoxide (8.43 ml) was added dropwise to a dichloromethane (40 ml) solution of oxalyl chloride (5.18 ml) at −78° C. and stirred for 15 minutes at the same temperature. Next, a dichloromethane (55 ml) solution of the product obtained in Example 2(2) (7.0 g) was added and the mixture was stirred for one hour at −78° C. Further, triethylamine (26.5 ml) was added and the mixture was stirred for one hour at 0° C. After the reaction, water was added, and the mixture was extracted with ethyl acetate, and the organic phase was washed with saturated aqueous sodium hydrogencarbonate solution and brine and then dried over magnesium sulfate. The solvent was evaporated in vacuo and the residue was purified by silica gel column chromatography to obtain 6-[1-[3-chloro-2-(3-pyridyl) indolyl]]hexanal (4.74 g).

(2) Synthesis of 6-[1-[3-chloro-2-(3-pyridyl) indolyl]] hexanal oxime

Pyridine (30 ml) and hydroxylamine hydrochloride (1.44 g) were added to ethanol (30 ml) solution of the product obtained in (1) (4.04 g) and the mixture was stirred at room temperature for 3 hours. After the reaction, the mixture was diluted with ethyl acetate, and the organic phase washed with water and brine, then dried over magnesium sulfate, after then the solvent was evaporated in vacuo to obtain 6-[1-[3-chloro-2-(3-pyridyl)indolyl]]hexanal oxime (4.39 g).

(3) Synthesis of 6-[1-[3-chloro-2-(3-pyridyl) indolyl]] hexylhydroxylamine

Under argon, sodium cyanoborohydride (2.21 g) was added to an acetic acid (30 ml) solution of the product obtained in (2)(2.05 g) at 0° C. and the mixture stirred at 0° C. for 45 minutes. After the reaction, saturated aqueous solution of sodium hydrogencarbonate was added at 0° C. and the mixture was extracted with ethyl acetate. The organic phase was washed with brine and was dried over magnesium sulfate, then the solvent was evaporated in vacuo and the residue was purified by silica gel column chromatography to obtain 6-[1-[3-chloro-2-(3-pyridyl) indolyl]]hexylhydroxylamine (961 mg).

(4) Synthesis of N-[6-[1-[3-chloro-2-(3-pyridyl) indolyl]] hexyl]-N-hydroxyurea

The product obtained in (3) (961 mg) was produced in the same way as Example 1(3) to obtain N-[6-[1-[3-chloro-2-(3-pyridyl)indolyl]]hexyl]-N-hydroxyurea (556 mg).

$^1$H-NMR (DMSO-d$_6$): δ1.03 (m, 4H), 1.30 (m, 2H), 1.48 (m, 2H), 3.17 (m, 2H), 4.14 (m, 2H), 6.18 (s, 2H), 7.21 (m,

1H), 7.32 (m, 1H), 7.56 (d, 1H), 7.61 (m, 1H)t 7.65 (d, 1H), 8.01 (m, 1H), 8.71 (d, 1H), 8.75 (d, 1H), 9.10 (s, 1H)

Example 5

N-[6-[1-[5-Chloro-2-(3-pyridyl)indolyl]]hexyl]-N-hydroxyurea (Compound 5)

5-Chloro-2-(3-pyridyl)indole instead of 2-(3-pyridyl)indole in Example 1(1), was used, and 6-bromohexyl alcohol instead of 12-bromododecyl alcohol, was used for the same way to obtain N-[6-[1-[5-chloro-2-(3-pyridyl)indolyl]]hexyl]-N-hydroxyurea.

$^1$H-NMR(DMSO-d$_6$): δ1.05(m, 4H), 1.30(m, 2H), 1.50 (m, 2H), 3.18(m, 2H), 4.20(m, 2H), 6.20(s, 2H), 6.63(s, 1H), 7.20(m, 1H), 7.56(m, 1H), 7.61(d, 1H), 7.64(d, 1H), 8.00(m, 1H), 8.66(m, 1H), 8.77(d, 1H), 9.11(s, 1H)

Example 6

N-Hydroxy-N-[8-[1-[2-(3-pyridyl)indolyl]]octyl]urea (Compound 6)

8-Bromooctyl alcohol instead of 12-bromododecyl alcohol in Example 1(1), was used and the same reaction performed for synthesis.

$^1$H-NMR (DMSO-d$_6$): δ1.05 (m, 8H), 1.39 (m, 2H), 1.52 (m, 2H), 3.24 (m, 2H), 4.20 (m, 2H), 6.20 (s, 2H), 6.62 (s, 1H), 7.07 (m, 1H), 7.19 (m, 1H), 7.58 (m, 2H), 7.58 (d, 1H), 7.98 (m, 1H), 8.64 (m, 1H), 8.76 (d, 1H), 9.15 (s, 1H)

Example 7

N-Hydroxy-N-[4-[1-[2-(3-pyridyl)indolyl]]butyl]urea (Compound 7)

4-Chlorobutanol instead of 6-bromohexyl alcohol in Example 2(1), was used and the same reactions were performed for synthesis.

$^1$H-NMR (DMSO-d$_6$): δ1.31 (m, 2H), 1.55 (m, 2H), 3.19 (m, 2H), 4.20 (m, 2H), 6.21 (s, 2H), 6.63 (s, 1H), 7.07 (m, 1H), 7.19 (m, 1H), 7.55 (m, 1H), 7.58 (m, 2H), 7.98 (m, 1H), 8.64 (m, 1H), 8.77 (d, 1H), 9.15 (s, 1H)

Example 8

N-[4-[1-[3-Chloro-2-(3-pyridyl)indolyl]]butyl]-N-hydroxyurea (Compound 8)

(1) Synthesis of 1-[4-(tert-butyldiphenylsilyloxy)butyl]-3-chloro-2-(3-pyridyl)indole N-Chlorosuccinimide (504 mg) was dissolved in an ethanol (9 ml) and water (1 ml) mixture of the 1-[4-(tert-butyldiphenylsilyloxy)butyl]-2-(3-pyridyl)indole (1.99 g) obtained in the same way as in Example 2(1), and the mixture was reacted at room temperature for 4.5 hours. After the reaction, water was added and the mixture was extracted with ethyl acetate, and the organic phase was washed with brine, then dried over magnesium sulfate, then the solvent was evaporated in vacuo and the residue was purified by silica gel column chromatography to obtain 1-[4-(tert-butyldiphenylsilyloxy)butyl]-3-chloro-2-(3-pyridyl)indole (1.24 g).

(2) Synthesis of N-[4-[1-[3-chloro-2-(3-pyridyl) indolyl]]butyl]-N-hydroxyurea

The product obtained in (1) (1.24 g) was reacted in the same way as in Example 2(2) to (4) to obtain N-[4-[1-[3-chloro-2-(3-pyridyl)indolyl]]butyl]-N-hydroxyurea (352 mg).

$^1$H-NMR (DMSO-d$_6$): δ1.26 (m, 2H), 1.49 (m, 2H), 3.16 (m, 2H), 4.15 (m, 2H), 6.24 (s, 2H), 7.21 (m, 1H), 7.31 (m, 1H), 7.56 (d, 1H), 7.62 (m, 1H), 7.68 (d, 1H), 8.00 (d, 1H), 8.72 (d, 1H), 8.75 (d, 1H), 9.15 (s, 1H)

Example 9

N-[6-[1-[3,5-Dichloro-2-(3-pyridyl)indolyl]]hexyl-]-N-hydroxyurea (Compound 9)

(1) Synthesis of N,O-bis-tert-butoxycarbonyl-6-[1-[3,5-dichloro-2-(3-pyridyl)indolyl]]hexylhydroxylamine N,O-Bis-tert-butoxycarbonyl-6-[1-[5-chloro-2-(3-pyridyl)indolyl]]hexylhydroxylamine (1.5 g) obtained in the same way as in Example 1(1) was treated in the same way as in Example 8(1) to obtain N,O-bis-(tert-butoxycarbonyl)-6-[1-[3,5-dichloro-2-(3-pyridyl) indolyl]] hexylhydroxylamine (1.13 g).

(2) Synthesis of N-[6-[1-[3,5-dichloro-2-(3-pyridyl) indolyl]]hexyl]-N-hydroxyurea The product obtained in (1) (1.13 g) was reacted in the same way as in Example 1(2) to (3) to obtain N-[6-[1-[3,5-dichloro-2-(3-pyridyl)indolyl]]hexyl]-N-hydroxyurea (425 mg).

$^1$H-NMR (DMSO-d$_6$): δ1.01 (m, 4H), 1.30 (m, 2H), 1.45 (m, 2H), 3.17 (m, 2H), 4.14 (m, 2H), 6.21 (s, 2H), 7.31 (m, 1H), 7.57 (d, 1H), 7.62 (m, 1H), 7.72 (d, 1H), 8.02 (d, 1H), 8.74 (m, 1H), 8.75 (d, 1H), 9.11 (s, 1H)

Example 10

N-[6-[1-[5-Chloro-3-methyl-2-(3-pyridyl) indolyl]]hexyl]-N-hydroxyurea (Compound 10)

5-Chloro-3-methyl-2-(3-pyridyl)indole instead of 5-chloro-2-(3-pyridyl)indole in Example 1(1), was used for the same manner to obtain N-[6-[1-[5-chloro-3-methyl-2-(3-pyridyl)indolyl]]hexyl]-N-hydroxyurea.

$^1$H-NMR (DMSO-d$_6$): 61.02 (m, 4H), 1.30 (m, 2H), 1.42 (m, 2H), 3.17 (m, 2H), 4.05 (m, 2H), 6.18 (s, 2H), 7.18 (m, 1H), 7.54 (d, 1H), 7.58 (m, 1H), 7.61 (d, 1H), 7.91 (m, 1H), 8.66 (d, 1H), 8.68 (m, 1H), 9.11 (s, 1H)

Example 11

N-Hydroxy-N-[10-[1-[2-(3-pyridyl)indolyl]]decyl]]urea (Compound 11)

10-Bromodecyl alcohol instead of 12-bromododecyl alcohol of Example 1(1), was used for the same manner to obtain N-hydroxy-N-[10-[1-[2-(3-pyridyl) indolyl]]decyl]urea.

$^1$H-NMR (DMSO-d$_6$): δ1.03–1.16 (m, 12H), 1.46 (m, 2H), 1.51 (m, 2H), 3.28 (m, 2H), 4.20 (m, 2H), 6.20 (s, 2H), 6.62 (s, 1H), 7.07 (m, 1H), 7.19 (m, 1H), 7.54 (m, 2H), 7.58 (d, 1H), 7.97 (m, 1H), 8.64 (m, 1H), 8.76 (d, 1H), 9.16 (s, 1H)

Example 12

N-[6-[1-[5-Fluoro-3-methyl-2-(3-pyridyl)indolyl]]hexyl]-N-hydroxyurea (Compound 12)

5-Fluoro-3-methyl-2-(3-pyridyl)indole instead of 2-(3-pyridyl)indole in Example 1(1), was used for the same manner to obtain N-[6-[1-[5-fluoro-3-methyl-2-(3-pyridyl)indolyl]]hexyl]-N-hydroxyurea.

$^1$H-NMR (DMSO-d$_6$): δ1.03 (m, 4H), 1.30 (m, 2H), 1.43 (m, 2H), 2.14 (s, 3H), 3.17 (t, 2H), 4.05 (t, 2H), 6.18 (s, 2H), 7.03 (m, 1H), 7.33 (m, 1H), 7.52 (m, 1H), 7.58 (m, 1H), 7.90 (m, 1H), 8.65 (d, 1H), 8.68 (m, 1H), 9.11 (s, 1H)

Example 13

N-Hydroxy-N-[6-[1-[3-methyl-2-(3-pyridyl)indolyl]]hexyl]urea (Compound 13)

3-Methyl-2-(3-pyridyl)indole instead of 5-chloro-2-(3-pyridyl)indole in Example 5, was used for the same manner to obtain N-hydroxy-N-[6-[1-[3-methyl-2-(3-pyridyl) indolyl]]hexyl]urea.

$^1$H-NMR (DMSO-d$_6$): δ 1.03 (m, 4H), 1.30 (m, 2H), 1.43 (m, 2H), 2.18 (s, 3H), 3.17 (m, 2H), 4.05 (m, 2H), 6.20 (s, 2H), 7.08 (m, 1H), 7.20 (m, 1H), 7.50 (m, 1H), 7.56 (d, 1H), 7.58 (d, 1H), 7.80 (m, 1H), 8.66 (m, 1H), 8.67 (d, 1H), 9.12 (s, 1H)

Example 14

N'-Cyclohexyl-N-hydroxy-N-[12-[1-[2-(3-pyridyl) indolyl]]dodecyl]urea (Compound 14)

Cyclohexylisocyanate instead of trimethylsilyl isocyanate in Example 1(3), was used to obtain N'-cyclohexyl-N-hydroxy-N-[12-[1-[2-(3-pyridyl) indolyl]]dodecyl]urea.

$^1$H-NMR (DMSO-d$_6$): δ1.04–1.36 (m, 22H), 1.46–1.70 (m, 8H), 3.34–3.37 (m, 1H), 3.28 (t, 1H), 4.20 (t, 1H), 6.43 (d, 1H), 6.62 (s, 1H), 7.07 (t, 1H), 7.19 (t, 1H), 7.53–7.55 (m, 2H), 7.58 (d, 1H), 7.97 (m, 1H), 8.64 (m, 1H), 8.76 (d, 1H), 9.12 (S, 1H)

Example 15

N-[6-[1-[5-Fluoro-3-methyl-2-(3-pyridyl)indolyl]-1-methyl]hexyl]-N-hydroxyurea (Compound 15)

(1) Synthesis of 6-[1-[5-fluoro-3-methyl-2-(3-pyridyl) indolyl]]hexanol

5-Fluoro-3-methyl-2-(3-pyridyl)indole instead of 2-(3-pyridyl)indole in Example 2, was used for the same manner as in Example 2(1) to (2) to obtain 6-[1-[5-fluoro-3-methyl-2-(3-pyridyl)indolyl]]hexanol.

(2) Synthesis of 6-[1-[5-fluoro-3-methyl-2-(3-pyridyl) indolyl]]hexanal

The product obtained in (1) (3.05 g) was treated in the same way as in Example 4(1) to obtain 6-[1-[5-fluoro-3-methyl-2-(3-pyridyl)indolyl]]hexanal (2.56 g).

(3) Synthesis of 6-[1-[5-fluoro-3-methyl-2-(3-pyridyl) indolyl]]-2-heptanol

Under argon, a 1M methylmagnesium in tetrahydrofuran (9 ml) was added to tetrahydrofuran (15 ml) solution of the product obtained in (2)(1.5 g) at 0° C. and the mixture reacted at room temperature for one hour. After the reaction, saturated aqueous ammonium chloride solution was added and the mixture was extracted with ethyl acetate, the organic phase was washed with a saturated aqueous of sodium hydrogencarbonate solution and brine, and dried over magnesium sulfate. The solvent was evaporated in vacuo and the residue was purified by silica gel column chromatography to obtain 6-[1-[5-fluoro-3-methyl-2-(3-pyridyl)indolyl]]-2-heptanol (1.76 g).

(4) Synthesis of N-[6-[1-[5-fluoro-3-methyl-2-(3 -pyridyl)indolyl]-1-methyl]hexyl]-N-hydroxyurea The product obtained in (3) (1.76 g) was treated in the same way as in Example 2(3) to (4) to obtain N-[6-[1-[5-fluoro-3-methyl-2-(3-pyridyl)indolyl]-1-methyl]hexyl]-N-hydroxyurea (723 mg).

$^1$H-NMR (DMSO-d$_6$): δ0.87–1.41 (m, 6H), 2.14 (s, 3H), 3.92 (m, 1H), 4.04 (m, 3H), 6.15 (s, 2H), 7.03 (m, 1H), 7.32 (m, 1H), 7.51 (m, 1H), 7.58 (m, 1H), 7.90 (m, 1H), 8.65 (d, 1H), 8.67 (m, 1H), 8.70 (s, 1H)

Example 16

6-[3-[1-[6-(N-Hydroxyureidohexyl)]-2-(3-pyridyl) indole]]hexanoic acid (Compound 16)

6-[3-[2-(3-Pyridyl)indolyl]]hexanoic acid (855 mg) was reacted in the same way as in Example 1(1) to (3) to obtain 6-[3-[1-[6-(N-hydroxyureidohexyl)]-2-(3-pyridyl)indole]] hexanoic acid (714 mg). The starting material [3-[2-(3-pyridyl)indole]]hexanoic acid was synthesized according to Japanese Unexamined Patent Publication (Kokai) No. 59-225181.

$^1$H-NMR (DMSO-d$_6$): δ1.26–1.34 (m, 6H), 1.53 (m, 6H), 1.63 (m, 2H), 2.24 (m, 2H), 2.83 (m, 2H), 3.28 (m, 2H), 3.96 (m, 1H), 6.21 (s, 2H), 7.03 (m, 1H), 7.13 (m, 1H), 7.37 (d, 1H), 7.53 (m, 1H), 7.56 (d, 1H), 7.81 (m, 1H), 8.56 (m, 1H), 8.82 (d, 1H), 9.17 (s, 1H), 11.28 (s, 1H)

Example 17

N-Hydroxy-N-[2-[1-[3-(3-pyridylmethyl)indolyl]]ethyl] urea (Compound 17)

(1) Synthesis of 3-(3-pyridylmethyl)indole

Under argon, indole (10 g) was dissolved in diethyl ether (100 ml), a 3M methylmagnesium bromide in diethyl ether solution (50 ml) was added at 0° C., and the mixture was stirred at room temperature for 2 hours. 3-Chloromethylpyridine hydrochloride (7 g) and benzene (90 ml) were added at 0° C. and the mixture was refluxed at 110° C. for 8 hours to evaporate the diethyl ether. After the reaction, a saturated ammonium chloride aqueous solution was added, and the mixture was extracted with ethyl acetate, the organic phase was washed with a saturated aqueous sodium hydrogencarbonate solution and brine, then dried over magnesium sulfate. The solvent was evaporated in vacuo and the residue was purified by silica gel column chromatography to obtain 3-(3-pyridylmethyl)indole (8.80 g).

(2) Synthesis of N-hydroxy-N-[2-[1-[3-(3-pyridylmethyl) indolyl]]ethyl]urea

The product obtained in (2) was treated in the same way as in Example 3(1) to (3) to obtain N-hydroxy-N-[2-[1-[3-(3-pyridylmethyl)indolyl]]ethyl]urea.

$^1$H-NMR (DMSO-d$_6$): δ3.67 (t, 1H), 4.04 (s, 1H), 4.26 (t, 1H), 6.36 (s, 2H), 6.97 (t, 2H), 7.12 (t, 1H), 7.24 (s, 1H), 7.27 (m, 1H), 7.42 (d, 1H), 7.44 (d, 1H), 7.63 (m, 1H), 8.37 (m, 1H), 8.55 (d, 1H), 9.52 (s, 1H)

Example 18

N-Hydroxy-N-[6-[1-[3-(3-pyridylmethyl)indolyl]]hexyl] urea (Compound 18)

The product obtained in Example 17(1) was treated in the same way as in Example 2(1) to (4) to obtain N-hydroxy-N-[6-[1-[3-(3-pyridylmethyl)indolyl]]hexyl]urea.

$^1$H-NMR (DMSO-d,): δ1.24 (m, 4H), 1.44 (m, 2H), 1.71 (m, 2H), 3.27 (m, 2H), 4.05 (s, 2H), 4.10 (m, 2H), 6.20 (s, 2H), 6.96 (m, 1H), 7.10 (m, 1H), 7.21 (s, 1H), 7.27 (m, 1H), 7.41 (d, 1H), 7.44 (d, 1H), 7.63 (m, 1H), 8.36 (m, 1H), 8.54 (d, 1H), 9.16 (s, 1H)

Example 19

N-Hydroxy-N-[2-[1-[3-(3-pyridyl)indolyl]]ethyl]urea (Compound 19)

3-(3-Pyridyl)indole instead of 2-(3-pyridyl)indole in Example 3(1), was used for the same reaction to obtain N-hydroxy-N-[2-[1-(3-(3-pyridyl) indolyl]]ethyl]urea.

The starting material 3-(3-pyridyl)indole was synthesized by the method described in European Patent No. 643059.

$^1$H-NMR (DMSO-d$_6$): δ 3.76 (t, 2H), 4.39 (t, 2H), 6.43 (s, 2H), 7.16 (m, 1H), 7.25 (m, 1H), 7.45 (m, 1H), 7.58 (d, 1H), 7.87–7.88 (m, 1H), 8.05 (m, 1H), 8.43 (m, 1H), 8.90 (d, 1H), 9.56 (s, 1H)

Example 20

N-Hydroxy-N-[2-[1-[2-methyl-3-(3-pyridyl)indolyl]]ethyl]urea (Compound 20)

2-Methyl-3-(3-pyridyl)indole instead of 2-(3-pyridyl)indole in Example 3(1), was used for the same reaction to obtain N-hydroxy-N-[2-[1-[2-methyl-3-(3-pyridyl)indolyl]]ethyl)urea.

The starting material 2-methyl-3-(3-pyridyl)indole was synthesized by the method described in European Patent No. 643059.

$^1$H-NMR (DMSO-d$_6$): δ2.51 (s, 3H), 3.68 (t, 2H), 4.37 (t, 2H), 6.46 (s, 2H), 7.09 (t, 1H), 7.19 (t, 1H), 7.50–7.53 (m, 3H), 7.87 (br.d, 2H), 8.52 (br.d, 1H), 8.68 (s, 1H), 9.62 (s, 1H)

Example 21

N-Hydroxy-N-[6-[1-[3-(3-pyridyl)indolyl]]hexyl]urea (Compound 21)

3-(3-Pyridyl)indole instead of 2-(3-pyridyl)indole in Example 3(1), was used and ethyl 6-bromohexanoate instead of ethyl 2-bromoacetate was used for the same reaction to obtain N-hydroxy-N-[6-[1-[3-(3-pyridyl)indolyl]]hexyl]urea.

$^1$H-NMR (DMSO-d$_6$): δ1.22–1.42 (m, 4H), 1.41–1.52 (m, 2H), 1.73–1.87 (m, 2H), 3.30 (t, 2H), 4.23 (t, 2H), 6.21 (s, 2H), 7.14 (t, 1H), 7.23 (t, 1H), 7.44 (m, 1H), 7.57 (d, 1H), 7.88 (d, 1H), 7.90 (s, 1H), 8.07 (m, 1H), 8.43 (m, 1H), 8.91 (d, 1H), 9.14 (s, 1H)

Example 22

N-Hydroxy-N-[6-[1-[5-fluoro-3-(3-pyridylmethyl)indolyl]]hexyl]urea (Compound 22)

5-Fluoroindole instead of indole of Example 17(1), was used and ethyl 6-bromohexanoate instead of ethyl 2-bromoacetate was used for the same reaction to obtain N-hydroxy-N-[6-[1-[5-fluoro-3-(3-pyridylmethyl)indolyl]]hexyl]urea.

$^1$H-NMR (DMSO-d$_6$): δ1.12–1.34 (m, 4H), 1.34–1.54 (m, 2H), 1.60–1.78 (m, 2H), 3.27 (t, 2H), 4.02, (s, 2H), 4.09 (t, 2H), 6.24 (s, 2H), 6.95 (m, 1H), 7.23 (m, 1H), 7.27 (m, 1H), 7.30 (s, 1H), 7.43 (m, 1H), 7.64 (d, 1H), 8.37 (d, 1H), 8.56 (slike, 1H), 9.16 (s, 1H)

Example 23

N-Hydroxy-N-[[3-[2-(3-pyridyl)indolyl]]methyl]urea (Compound 23)

(1) Synthesis of 3-[2-(3-pyridyl)indole]aldehyde

Under argon, phosphorus oxychloride (2.24 ml) was added to dimethylformamide (3.4 ml) at 0° C. and the mixture was stirred for one hour at 0° C. A dimethylformamide (6.8 ml) solution of 2-(3-pyridyl) indole (4.24 g) was added dropwise at 0° C. and the mixture was stirred at room temperature for 4 hours. After the reaction, a saturated aqueous sodium hydrogencarbonate solution was added at 0° C. and the mixture was extracted with ethyl acetate. The organic phase was washed with brine, then dried over magnesium sulfate, then the solvent was evaporated in vacuo and the residue was recrystallized by methanol to obtain 3-[2-(3-pyridyl)indole]aldehyde (4.32 g).

(2) Synthesis of N-hydroxy-N-[3-[2-(3-pyridyl)indolyl]methyl]urea

The product obtained in (1) (2.5 g) was reacted in the same way as in Example 4(2) to (4) to obtain N-hydroxy-N-[3-[2-(3-pyridyl)indolyl]methyl]urea (760 mg).

$^1$H-NMR (DMSO-d$_6$): δ4.77 (s, 2H), 6.32 (s, 2H), 7.03 (m, 1H), 7.15 (m, 1H), 7.39 (d, 1H), 7.51 (m, 1H), 7.77 (d, 1H), 8.19 (m, 1H), 8.58 (m, 1H), 9.00 (d, 1H), 9.30 (s, 1H), 11.44 (s, 1H)

Example 24

N-Hydroxy-N-[3-[3-[1-methyl-2-(3-pyridyl)indolyl]]-2-propenyl]urea (Compound 24)

(1) Synthesis of 1-methyl-2-(3-pyridyl)indole

Under argon, a dimethylformamide (30 ml) solution of 2-(3-pyridyl)indole (3.07 g) was added to dimethylformamide (20 ml) in which 60% sodium hydride (0.76 g) was suspended and the mixture was stirred at room temperature for 30 minutes. Methyl iodide (1.2 ml) was added at 0° C. and the mixture was stirred at room temperature for one hour. The mixture was reacted at 0° C., then a saturated aqueous sodium hydrogencarbonate solution was added and the mixture was extracted with ethyl acetate. The organic phase was washed with brine and dried over magnesium sulfate, then the solvent was evaporated in vacuo and the residue was purified by silica gel column chromatography to obtain 1-methyl-2-(3-pyridyl)indole (1.72 g).

(2) Synthesis of 3-[1-methyl-2-(3-pyridyl) indole] aldehyde

The product obtained in (1) (1.72 g) was reacted in the same way as in Example 23(1) to obtain 3-[1-methyl-2-(3-pyridyl)indole]aldehyde (1.82 g).

(3) Synthesis of methyl 3-[3-[1-methyl-2-(3-pyridyl)indolyl]]acrylate

The product obtained in (2)(1.82 g) and methyl (triphenylphosphoranylidene)acetate (2.83 g) were refluxed in toluene (50 ml) at 140° C. for 45 hours. After the reaction, the solvent was evaporated in vacuo and the residue was purified by silica gel column chromatography to obtain methyl 3-[3-[1-methyl-2-(3-pyridyl)indolyl]]acrylate (3.95 g).

(4) Synthesis of 3-[3-fl-methyl-2-(3-pyridyl)indoly]]-2-propenol

Under argon, a 1M diisobutylaluminum hydride in toluene (7.2 ml) was added dropwise to toluene (20 ml) solution of the product obtained in (3) (3.95 g) at −78° C. and the mixture stirred at −78° C. After the reaction, diethyl ether (68 µl) and water (68 µl) were added and the mixture was stirred at 0° C. for 15 minutes, then an excess of magnesium sulfate was added and the mixture was further stirred for 20 minutes. The insoluble matters were filtered out, then the solvent was evaporated and the residue was purified by silica gel column chromatography to obtain 3-[3-[1-methyl-2-(3-pyridyl)indolyl]]-2-propenol (500 mg).

(5) Synthesis of 3-[3-[1-methyl-2-(3-pyridyl)indolyl]] acrylaldehyde

Manganese dioxide (2.5 g) was suspended in a methylene chloride (5 ml) solution of the product obtained in (4) (500 mg) and the mixture stirred at room temperature for 5 hours. After the reaction, the mixture was filtered through Celite and the solvent was evaporated in vacuo to obtain 3-[3-[1-methyl-2-(3-pyridyl)indolyl]]acrylaldehyde (389 mg).

(6) Synthesis of N-hydroxy-N-[3-[3-[1-methyl-2-(3-pyridyl)indolyl]]-2-propenyl]urea The product obtained in (5) was treated in the same way as in Example 4(2) to (4) to obtain N-hydroxy-N-[3-[3-[1-methyl-2-(3-pyridyl)indolyl]]-2-propenyl]urea.

$^1$H-NMR (DMSO-d$_6$): δ2.77 (s, 3H), 4.26 (d, 2H), 5.31 (br.s, 2H), 6.22 (m, 1H), 6.47 (d, 1H), 7.17 (d, 1H), 7.19 (d,

1H), 7.34 (t, 1H), 7.44 (m, 1H), 7.65 (m, 1H), 7.91 (d, 1H), 8.32 (s, 1H), 8.55 (d, 1H), 10.41 (br.s, 1H)

Example 25

N-Hydroxy-N-[3-[3-[1-(3-pyridylmethyl)indolyl]]-2-proipenyl]urea (Compound 25)

(1) Synthesis of 1-(3-pyridylmethyl)indole

Under argon, a dimethylformamide (50 ml) solution of indole (18 g) was added into dimethylformamide (350 ml) in which 60% sodium hydride (7.9 g) was suspended, and the mixture was stirred at room temperature for 30 minutes. A dimethylformamide (100 ml) solution of 3-chloromethylpyridine hydrochloride (25 g) was added at 0° C. and the mixture stirred at room temperature for 18 hours. After the reaction, a saturated aqueous sodium hydrogencarbonate solution was added at 0° C. and the mixture was extracted with ethyl acetate. The organic phase was washed with brine and dried over magnesium sulfate, then the solvent was evaporated in vacuo and the residue was purified by silica gel column chromatography to obtain 1-(3-pyridylmethyl)indole (31.9 g).

(2) Synthesis of 3-[1-(3-pyridylmethyl)indolyl]aldehyde

The product obtained in (1) was processed in the same way as in Example 23(1) to obtain 3-[1-(3-pyridylmethyl)indole]aldehyde.

(3) Synthesis of N-hydroxy-N-[3-[3-[1-(3-pyridylmethyl)indolyl]]-2-propenyl]urea The product obtained in (2) was treated in the same way as in Example 24(3) to (6) to obtain N-hydroxy-N-[3-[3-[1-(3-pyridylmethyl)indolyl]]-2-propenyl]urea.

$^1$H-NMR (DMSO-$d_6$): δ4.10 (d, 2H), 5.44 (s, 2H), 6.13 (m, 1H), 6.33 (s, 2H), 6.67 (d, 1H), 7.08 (t, 1H), 7.15 (t, 1H), 7.31 (m, 1H), 7.51 (d, 1H), 7.56 (m, 1H), 7.67 (s, 1H), 7.78 (d, 1H), 8.44 (m, 1H), 8.53 (d, 1H), 9.30 (s, 1H)

Example 26

N-Hydroxy-N-[3-[1-(3-pyridylmethyl)indolyl]methyl]urea (Compound 26)

The product obtained in Example 25(2) was treated in the same way as in Example 4(2) to (4) to obtain N-hydroxy-N-[3-[1-(3-pyridylmethyl)indolyl]methyl]urea.

$^1$H-NMR (DMSO-$d_6$): δ4.64 (s, 2H), 5.43 (s, 2H), 6.23 (s, 2H), 7.00 (t, 1H), 7.10 (t, 1H), 7.32 (m, 1H), 7.45 (d, 1H), 7.46 (s, 1H), 7.58 (m, 1H), 7.66 (d, 1H), 8.45 (m, 1H), 8.53 (m, 1H), 9.22 (s, 1H)

Example 27

N-Hydroxy-N-[4-[3-[1-(3-pyridylmethyl) indolyl]] methylbenzyl]urea (Compound 27)

(1) Synthesis of methyl 4-[3-[1-(3-pyridylmethyl)indolyl]]methylbenzoate

A methanol (20 ml) solution of 4-[3-[1-(3-pyridylmethyl) indolyl]]methyl benzoic acid (1.27 g) was refluxed in the presence of concentrated sulfuric acid (0.5 ml) at 85° C. for 3 hours. After the reaction, a saturated aqueous sodium hydrogencarbonate solution was added at 0° C. and the mixture was extracted with ethyl acetate. The organic phase was washed with brine and dried over magnesium sulfate, then the solvent was evaporated in vacuo and the residue was purified by silica gel column chromatography to obtain methyl 4-methyl-[3-[1-(3-pyridylmethyl)indolyl]] methylbenzoate (547 mg). The starting material 4-[3-[1-(3-pyridylmethyl) indolyl]]methylbenzoic acid was synthesized by the method described in Japanese Unexamined Patent Publication (Kokai) No. 59-225181.

(2) Synthesis of N-hydroxy-N-[4-methyl-[3-[1-(3-pyridylmethyl)indolyl]]benzyl]urea The product obtained in (1) (275 mg) was processed in the same way as in Example 3(2) to (3) to obtain N-hydroxy-N-[4-methyl-[3-[1-(3-pyridylmethyl) indolyl]]benzyl]urea (53 mg).

$^1$H-NMR (CDCl$_3$): 4.07 (s, 2H), 4.65 (s, 2H), 4.95 (s, 2H), 5.15 (br.s, 2H), 6.80 (s, 1H), 7.02–7.24 (m, 9H), 7.58 (d, 1H), 7.97 (m, 1H), 8.24 (m, 1H)

Example 28

N-Hydroxy-N-[3-[1-[3-(3-pyridyl propyl]indolyl]methyl] urea (Compound 28)

3-(3-Pyridyl)propyl bromide instead of 3-chloromethylpyridine hydrochloride in Example 25(1), was used for the manner in the same way as in Example 26 to obtain N-hydroxy-N-[3-[1-[3-(3-pyridyl) propyl]indolyl] methyl]urea.

The starting material 3-(3-pyridyl)propylbromide was obtained by the following method. 3-(3-pyridyl) propylpropanol was stirred in methylene chloride with carbon tetrabromide and triphenylphosphine at room temperature for 30 minutes. After the reaction, a saturated aqueous sodium hydrogencarbonate solution was added at 0° C. and the mixture was extracted with methylene chloride and ethyl acetate. The organic phase was washed with brine and dried over magnesium sulfate, then the solvent was evaporated in vacuo and the residue was purified by silica gel column chromatography.

$^1$H-NMR (DMSO-$d_6$): δ2.07 (m, 2H), 2.60 (m, 2H), 4.16 (m, 2H), 4.62 (s, 2H), 6.21 (s, 2H), 6.99 (m, 1H), 7.11 (m, 1H), 7.28–7.31 (m, 1H), 7.39 (d, 1H), 7.60–7.65 (m, 1H), 7.64 (d, 1H), 8.38–8.40 (m, 1H), 8.42 (d, 1H), 9.20 (s, 1H)

Example 29

N-Hydroxy-N-[3-[5-bromo-1-(3-pyridylmethyl)indolyl] methyl]urea (Compound 29)

5-Bromoindole instead of indole in Example 25(1), was used for the same processing as in Example 26 to obtain N-hydroxy-N-[3-[5-bromo-1-(3-pyridylmethyl)indolyl] methyl]urea.

$^1$H-NMR (DMSO-$d_6$): 54.53 (s, 2H), 5.37 (s, 2H), 6.22 (s, 2H), 7.14 (m, 1H), 7.24 (m, 1H), 7.38 (d, 1H), 7.46 (s, 1H), 7.49 (d, 1H), 7.77 (d, 1H), 8.39 (d, 1H), 8.44 (d, 1H), 9.20 (s, 1H)

Example 30

N-Hydroxy-N-[3-[2-methyl-1-(3-pyridylmethyl) indolyl] methyl]urea (Compound 30)

2-Methylindole instead of indole in Example 25(1), was used for the same processing as in Example 26 to obtain N-hydroxy-N-[3-[2-methyl-1-(3-pyridylmethyl)indolyl] methyl]urea.

$^1$H-NMR (DMSO-$d_6$): δ2.38 (s, 3H), 4.66 (s, 2H), 5.46 (s, 2H), 6.19 (s, 2H), 7.30 (m, 2H), 7.34 (m, 2H), 7.36 (d, 1H), 7.63 (d, 1H), 8.35 (d, 1H), 8.43 (d, 1H), 9.16 (s, 1H)

Example 31

N-Hydroxy-N-[1-[3-[1-(3-pyridylmethyl) indolyl]]ethyl] urea (Compound 31)

(1) Synthesis of 1-[3-[1-(3-pyridylmethyl) indolyl]] ethanol

The product obtained in Example 25(2) (2.5 g) was processed in the same way as in Example 15(3) to obtain 1-[3-[1-(3-pyridylmethyl)indolyl]]ethanol (2.8 g).

(2) Synthesis of N-hydroxy-N-[1-[3-[1-(3-pyridylmethyl) indolyl]]ethyl]urea

The compound obtained in (1) was processed in the same way as in Example 24(5) to (6) to obtain N-hydroxy-N-[1-[3-[1-(3-pyridylmethyl)indolyl]]ethyl]urea.

$^1$H-NMR (DMSO-$d_6$): δ1.48 (d, 3H), 5.43 (s, 2H), 5.65 (m, 1H), 6.22 (s, 2H), 6.99 (t, 1H), 7.08 (t, 1H), 7.31 (m, 1H), 7.41 (d, 1H), 7.48 (s, 1H), 7.57 (d, 1H), 7.66 (d, 1H), 8.45 (m, 1H), 8.52 (d, 1H), 8.88 (s, 1H)

Example 32

N-Hydroxy-N-[3-[5-fluoro-1-(3-pyridylmethyl) indolyl]methyl]urea (Compound 32)

5-Fluoroindole instead of indole of Example 25(1), was used and the same processing was performed to obtain N-hydroxy-N-[3-[5-fluoro-1-(3-pyridylmethyl)indolyl]methyl]urea.

$^1$H-NMR (DMSO-$d_6$): δ4.59 (s, 2H), 5.44 (s, 2H), 6.27 (s, 2H), 6.95 (m, 1H), 7.32 (m, 1H), 7.40 (m, 1H), 7.46 (m, 1H), 7.55 (s, 1H), 7.58 (dlike, 1H), 8.46 (m, 1H), 8.53 (d, 1H), 9.25 (s, 1H)

Example 33

N-Hydroxy-N-[5-[1-(3-pyridylmethyl) indolyl]] methylurea (Compound 33)

(1) Synthesis of indole-5-carboxylic acid methyl ester

A methanol (200 ml) solution of indole-5-carboxylic acid (5.15 g) was refluxed in the presence of concentrated sulfuric acid (3 ml) at 85° C. for 4.5 hours. After the reaction, saturated aqueous sodium hydrogencarbonate solution was added at 0° C. and the mixture was extracted with ethyl acetate. The organic phase was washed with brine and dried over magnesium sulfate, then the solvent was evaporated in vacuo and the residue was purified by silica gel column chromatography to obtain indole-5-carboxylic acid methyl ester (4.8 g).

(2) Synthesis of 1-(3-pyridylmethyl)indole-5-carboxylic acid methyl ester

The product obtained in (1) (9.84 g) was processed in the same way as in Example 25(1) to obtain 1-(3-pyridylmethyl)indole-5-carboxylic acid methyl ester (12.76 g).

(3) Synthesis of 5-[1-(3-pyridylmethyl)indolyl]methanol

The product obtained in (2) (1.5 g) was processed in the same way as in Example 3(2) to obtain 5-[1-(3-pyridylmethyl)indolyl]methanol (1.32 g).

(4) Synthesis of 1-(3-pyridylmethyl)indole-5-aldehyde

Manganese dioxide (44.5 g) was suspended in a methylene chloride solution (60 ml) of the product obtained in (3)(8.98 g) and the mixture was stirred at room temperature for 7 hours. After the reaction, the mixture was filtered through Celite and the solvent was evaporated in vacuo to obtain 1-(3-pyridylmethyl)indole-5-aldehyde (8.25 g).

(5) Synthesis of 1-(3-pyridylmethyl)indole-5-aldehyde oxime

Pyridine (15 ml) and hydroxylamine hydrochloride (2.4 g) were added to ethanol (15 ml) solution of the product obtained in (4) (5.3 g) and the mixture was stirred at room temperature for 4 hours. After the reaction, the mixture was diluted with ethyl acetate, successively washed with water and brine, then dried over magnesium sulfate, then the solvent was evaporated in vacuo to obtain 1-(3-pyridylmethyl)indole-5-aldehyde oxime (6.21 g).

(6) Synthesis of N-hydroxy-N-[5-[1-(3-pyridylmethyl)indolyl]methyl]urea

The product obtained in (5) was processed in the same way as in Example 4(3) to (4) to obtain N-hydroxy-N-[5-[1-(3-pyridylmethyl)indolyl]methyl]urea (86.5 mg).

$^1$H-NMR (DMSO-$d_6$): δ4.54 (s, 2H), 5.44 (s, 2H), 6.26 (s, 2H), 6.45 (d, 1H), 7.05 (d, 1H), 7.30 (m, 1H), 7.42 (d, 1H), 7.45 (s, 1H), 7.51 (d, 1H), 7.54 (d, 1H), 8.43 (d, 1H), 8.49 (s, 1H), 9.21 (s, 1H)

Example 34

N-[3-[5-[1,3-Dimethyl-2-(3-pyridyl)indolyl]]-2-propenyl]-N-hydroxyurea (Compound 34)

(1) Synthesis of methyl 4-[1-(3-pyridyl)propylenehydradino]benzoate

4-Hydradinobenzoic acid (28.1 g) and 3-propionylpyridine (25 g) were stirred in methanol (500 ml) solvent at 60° C. for 2 hours. The reaction solution was cooled to 0° C., then concentrated sulfuric acid (40 ml) was added and the mixture refluxed at 85° C. for 2.5 hours. After the reaction, a saturated aqueous sodium hydrogencarbonate solution was added at 0° C., then the mixture was extracted with ethyl acetate, washed with brine, and was dried over magnesium sulfate and the solvent was evaporated in vacuo to obtain methyl 4-[1-(3-pyridyl)propylenehydradino]benzoate.

(2) Synthesis of 3-[2-(5-carboxy-3-methyl)indoly]pyrridinium acetate

An acetic acid (1000 ml) solution of the product obtained in (1) (81.62 g) was refluxed in a boron trifluoride-diethyl ether complex (350 ml) at 120° C. for 37.5 hours. After the reaction, the precipitate was filtered out and then dried to obtain 3-[2-(5-carboxy-3-methyl)indoly]pyrridinium acetate (206 g).

(3) Synthesis of methyl 3-methyl-2-(3-pyridyl)indole-5-carboxylate

The product obtained (2) was treated in the same way as in Example 33(1) to obtain methyl 1,3-dimethyl-2-(3-pyridyl)indole-5-carboxylate.

(4) Synthesis of methyl 1,3-dimethyl-2-(3-pyridyl)indole-5-carboxylate

The product obtained in (3) (55 g) was treated in the same way as in Example 24(1) to obtain methyl 1,3-dimethyl-2-(3-pyridyl)indole-5-carboxylate (48 g).

(5) Synthesis of 1,3-dimethyl-2-(3-pyridyl)indole-5-methanol

The product obtained in (4) was treated in the same way as in Example 3(2) to obtain 1,3-dimethyl-2-(3-pyridyl)indole-5-methanol.

(6) Synthesis of 1,3-dimethyl-2-(3-pyridyl)indole-5-aldehyde

The product obtained in (5) was reacted in the same way as in Example 24(5) to obtain 1,3-dimethyl-2-(3-pyridyl)indole-5-aldehyde.

(7) Synthesis of 5-[1,3-dimethyl-2-(3-pyridyl) indolyl]-2-propenylcarboxylate methyl ester The product obtained in (6) (1.9 g) and methyl (triphenylphosphoranylidene)acetate (2.79 g) were refluxed in toluene (120 ml) at 130° C. for 24 hours. After the reaction, the solvent was evaporated in vacuo and the residue was purified by silica gel column chromatography to obtain methyl 5-[1,3-dimethyl-2-(3-pyridyl)indolyl]-2-propenylcarboxylate (3.83 g).

(8) Synthesis of N-[3-[5-[1,3-dimethyl-2-(3-pyridyl)indolyl]]-2-propenyl]-N-hydroxyurea The product obtained in (7) was treated in the same way as in Example 24(4) to (6) to obtain N-[5-[3-[1,3-dimethyl-2-(3-pyridyl)indolyl]]-2-propenyl]-N-hydroxyurea.

¹H-NMR (DMSO-d₆):δ 2.26 (s, 3H), 3.33 (s, 3H), 4.11 (d, 2H), 6.22 (m, 1H), 6.34 (s, 2H), 6.65 (d, 1H), 7.39–8.79 (m, 7H), 9.32 (s, 1H)

Example 35

N-[5-[1,3-Dimethyl-2-(3-pyridyl)indolyl]methyl]-N-hydroxyurea (Compound 35)

(1) Synthesis of 5-[1,3-dimethyl-2-(3-pyridyl) indolyl]methylhydroxylamine

The product obtained from Example 34(6) was reacted in the same way as in Example 4(2) to (3) to obtain 5-[1,3-dimethyl-2-(3-pyridyl)indolyl]methylhydroxylamine.

(2) Synthesis of N-[5-[1,3-dimethyl-2-(3-pyridyl)indolyl]methyl]-N-hydroxyurea

The product obtained in (1) (1 g) was dissolved in ethyl acetate (11 ml), potassium cyanate (334 mg) dissolved in water (1.2 ml) was added, and the mixture was stirred at room temperature for 30 minutes. After the reaction, a saturated aqueous sodium hydrogencarbonate solution was added at 0° C. and the mixture was extracted with ethyl acetate. The organic phase was washed with brine, then dried over magnesium sulfate, then the solvent was evaporated in vacuo and the residue was recrystallized by chloroform to obtain N-[5-[1,3-dimethyl-2-(3-pyridyl)indolyl]methyl]-N-hydroxyurea (734 mg).

¹H-NMR (DMSO-d₆):δ 2.22 (s, 3H), 3.60 (s, 3H), 4.63 (s, 2H), 6.31 (s, 1H), 7.18 (m, 1H), 7.41 (d, 1H), 7.48 (m, 1H), 7.57 (m, 1H), 7.91 (m, 1H), 8.65 (m, 1H), 8.68 (d, 1H), 9.26 (s, 1H)

Example 36

Ethyl 5-[1-[5-(N-hydroxyureidomethyl)-3-methyl-2-(3-pyridyl)indolyl]]pentanate (Compound 36)

(1) Synthesis of 5-[3-methyl-2-(3-pyridyl) indolyl]methanol

The product obtained in Example 34(3) (5.85 g) was treated in the same way as in Example 3(2) to obtain 5-[3-methyl-2-(3-pyridyl)indolyl]methanol (4.59 g).

(2) Synthesis of 5-tert-butyldiphenylsilyloxymethyl-3-methyl-2-(3-pyridyl)indole Under argon, tert-butyldiphenylchlorosilane (3.55 g) was stirred in the product obtained in (1) (3.57 g) in dimethylformamide (17 ml) in the presence of imidazole (2.04 g) at room temperature for 1 hour. After the reaction, water was added and the mixture was extracted with ethyl acetate. The organic phase was washed with brine and dried over magnesium sulfate, then the solvent was evaporated in vacuo and the residue was purified by silica gel column chromatography to obtain 5-tert-butyldiphenylsilyloxymethyl-3-methyl-2-(3-pyridyl)indole (7.15 g).

(3) Synthesis of ethyl 5-[1-[5-tert-butyldiphenylsilyloxymethyl-3-methyl-2-(3-pyridyl)indolyl]]pentanate The product obtained from (2)(2.99 g) instead of 12-(3-pyridyl)indole in Example 1(1), was used and 5-bromopentancarboxylic acid instead of the 12-N,O-bis-(tert-butoxycarbonyl)aminododecyl bromide, was used for the same manner to obtain ethyl 5-[1-(5-tert-butyldiphenylsilyloxymethyl-3-methyl-2-(3-pyridyl)indolyl]]pentanate (2.35 g).

(4) Synthesis of ethyl 5-[1-[5-(N-hydroxyureidomethyl)-3-methyl-2-(3-pyridyl)indolyl]]pentanate The product obtained in (3) (1.05 g) was treated in the same way as in Example 2(2) to (4) to obtain ethyl 5-[1-[5-(N-hydroxyureidomethyl)-3-methyl-2-(3-pyridyl)indolyl]]pentanate (859 mg).

¹H-NMR (DMSO-d₆):δ 1.18 (t, 3H), 1.24–1.43 (m, 4H), 2.07 (t, 2H), 2.10 (s, 3H), 3.80 (m, 2H), 4.04 (m, 2H), 4.83 (s, 2H), 5.56 (br.s, 2H), 7.21 (d, 1H), 7.31 (m, 1H), 7.39 (m, 1H), 7.47 (m, 1H), 7.54–7.68 (m, 2H), 8.47 (m, 1H), 10.62 (s, 1H)

Example 37

5-[1-[5-(N-Hydroxyureidomethyl)-3-methyl-2-(3-pyridyl)indolyl]]pentanoic acid (Compound 37)

The product obtained in Example 36(4)(381 mg) was stirred in a 3N aqueous sodium hydroxide solution (5 ml) and tetrahydrofuran (5 ml) at room temperature for 2.5 hours. After the reaction, a saturated aqueous sodium hydrogencarbonate solution was added and the mixture was extracted with ethyl acetate. The organic phase was washed with brine and dried over magnesium sulfate, then the solvent was evaporated in vacuo and the residue was purified by silica gel column chromatography to obtain 5-[1-[5-(N-hydroxyureidomethyl)-3-methyl-2-(3-pyridyl)indolyl]]pentanoic acid (230 mg).

¹H-NMR (DMSO-d₆):δ 1.24 (m, 2H), 1.45 (m, 2H), 2.02 (t, 2H), 2.16 (s, 3H), 4.06 (t, 2H), 4.61 (s, 2H), 6.29 (s, 2H), 7.15 (m, 1H), 7.44 (d, 1H), 7.47 (s, 1H), 7.57 (m, 1H), 7.88 (m, 1H), 8.63 (d, 1H), 8.66 (m, 1H), 9.25 (s, 1H), 11.94 (br.s, 1H)

Example 38

N-[3-[5-[1,3-Dimethyl-2-(3-pyridyl)indolyl]propyl]]-N-hydroxyurea (Compound 38)

(1) Synthesis of methyl 3-[5-[1,3-dimethyl-2-(3-pyridyl)indolyl]]propionate

10% Pd—C (1.00 g) was added to a methanol (100 ml) solution of the compound obtained in Example 34(7) (9.00 g) and under a hydrogen atmospheres of 4.5 pressures the mixture was shaken for 15 hours. After the reaction, the catalyst was filtered out and the solvent was evaporated in vacuo to obtain methyl 3-[5-[1,3-dimethyl-2-(3-pyridyl)indolyl]propionate (8.33 g).

(2) Synthesis of 3-[5-[1,3-dimethyl-2-(3-pyridyl)indolyl]] propanol

The compound obtained in (1) (9.70 g) was processed in the same way as Example 3(2) to obtain 3-[5-[1,3-dimethyl-2-(3-pyridyl)indolyl]]propanol (8.23 g).

(3) Synthesis of N-[3-[5-[1,3-dimethyl-2-(3-pyridyl)indolyl]propyl]]-N-hydroxyurea The compound obtained in (2) was reacted in the same way as in Example 4(1) to (4) to obtain N-[3-[5-[1,3-dimethyl-2-(3-pyridyl)indolyl]propyl]]-N-hydroxyurea.

¹H-NMR (DMSO-d₆): δ1.83 (m, 2H), 2.19 (s, 3H), 2.68 (t, 2H), 3.34 (t, 2H), 3.57 (s, 3H), 6.24 (s, 2H), 7.08 (d, 1H), 7.36 (d, 1H), 7.37 (s, 1H), 7.56 (m, 1H), 7.89 (m, 1H), 8.63 (m, 1H), 8.66 (d, 1H), 9.24 (s, 1H)

Example 39

N-Hydroxy-N-[5-[1-[3-(3-pyridyl)propyl]indolyl]methyl]urea (Compound 39)

The product of Example 33(1) instead of indole in Example 28, was used for the same manner to obtain N-hydroxy-N-[5-[1-[3-(3-pyridyl)propyl]indolyl]methyl]urea.

¹H-NMR (DMSO-d₆):δ 2.20 (m, 2H), 2.50 (m, 2H), 4.16 (m, 2H), 4.76 (s, 2H), 5.21 (br.s, 2H), 6.23 (d, 1H), 6.94 (d,

1H), 6.97 (m, 1H), 7.15 (d, 1H), 7.20 (m, 1H), 7.23 (s, 1H), 7.40 (s, 1H), 7.52 (d, 1H), 8.02 (m, 1H), 9.36 (br.s, 1H)

Example 40

N-Hydroxy-N-[5-[1-methyl-3-(3-pyridyl)indolyl]methyl] urea (Compound 40)

(1) Synthesis of ethyl 3-(3-pyridyl)indole-5-carboxylate

4-Hydradinobenzoic acid (18 g) and 3-(2-methoxyethenyl)pyridine(16 g) were stirred in concentrated hydrochloric acid (100 ml) at 100° C. for 2.5 hours. The reaction solution was cooled to 0° C., then ethanol (300 ml) was added and the mixture was refluxed at 105° C. for 3 hours. After the reaction, the mixture was neutralized at 0° C. with a sodium hydroxide aqueous solution, was extracted with ethyl acetate, washed with brine, and dried over magnesium sulfate, and the solvent was evaporated in vacuo to obtain ethyl 3-(3-pyridyl)indole-5-carboxylate (12.6 g).

The starting material 3-(2-methoxyethenyl)pyridine was synthesized by the method described in European Patent No. 643059.

(2) Synthesis of 1-methyl-[3-(3-pyridyl)indol]-5-aldehyde

The product obtained in (1) was treated in the same way as in Example 34(4) to (6) to obtain 1-methyl-[3-(3-pyridyl)indol]-5-aldehyde.

(3) Synthesis of N-hydroxy-N-[5-[1-methyl-3-(3-pyridyl)indolyl]methyl]urea

The product obtained in (2) was treated in the same way as in Example 4(2) to (4) to obtain N-hydroxy-N-[5-[1-methyl-3-(3-pyridyl)indolyl]methyl]urea.

$^1$H-NMR (DMSO-$d_6$):δ 3.84 (s, 3H), 4.63 (s, 2H), 6.32 (s, 2H), 7.20 (d, 1H), 7.44–7.46 (m, 1H), 7.47 (d, 1H), 7.80 (m, 2H), 8.03 (m, 1H), 8.43 (m, 1H), 8.90 (m, 1H), 9.29 (s, 1H)

Example 41

N-[1-[5-[1,3-Dimethyl-2-(3-pyridyl)indolyl]]ethyl]-N-hydroxyurea (Compound 41)

The product obtained in Example 34(6) was treated in the same way as in Example 31(1) to (2) to obtain N-(1-[5-[1,3-dimethyl-2-(3-pyridyl)indolyl]]ethyl]-N-hydroxyurea.

$^1$H-NMR (DMSO-$d_6$):δ 1.48 (d, 3H), 2.21 (s, 3H), 3.59 (s, 3H), 5.40–5.45 (m, 1H), 6.22 (s, 2H), 7.24 (m, 1H), 7.37 (d, 1H), 7.51 (s, 1H), 7.57 (m, 1H), 7.91 (m, 1H), 8.31 (s, 1H), 8.65 (m, 1H), 8.67 (d, 1H), 8.95 (s, 1H)

Example 42

N-Hydroxy-N-[1-[5-[1-(3-pyridylmethyl) indolyl]]ethyl] urea (Compound 42)

(1) Synthesis of 1-[5-[1-(3-pyridylmethyl) indolyl]]ethanol

The product obtained in Example 33(4) was treated in the same way as in Example 15(3) to obtain 1-[5-[1-(3-pyridylmethyl)indolyl]]ethanol.

(2) Synthesis of 1-[5-[1-(3-pyridylmethyl) indolyl]] ethanal oxime

The product obtained in (1) was treated in the same way as in Example 33(4) to (5) to obtain 1-[5-[1-(3-pyridylmethyl)indolyl]]ethanal oxime.

(3) Synthesis of 1-[5-[1-(3-pyridylmethyl) indolyl]] ethylhydroxylamine

The product obtained in (2) (2.2 g) was dissolved in ethanol (32 ml) and concentrated sulfuric acid (4 ml) was added dropwise at 0° C. Sodium cyanoborohydride (3.6 g) was added at 0° C. and the mixture was stirred at room temperature for 1.5 hours. After the reaction, a dilute aqueous sodium hydroxide solution was added for neutralization, then the mixture was extracted with methylene chloride, successively washed with water and brine, and dried over magnesium sulfate. The solvent was evaporated in vacuo to obtain 1-[5-[1-(3-pyridylmethyl)indolyl]] ethylhydroxylamine (1.7 g).

(4) Synthesis of N-hydroxy-N-[1-[5-[1-(3-pyridylmethyl) indolyl]]ethyl]urea

The product obtained in (3) was treated in the same way as in Example 1(3) to obtain N-hydroxy-N-[1-[5-[1-(3-pyridylmethyl)indolyl]]ethyl]urea.

$^1$H-NMR (DMSO-$d_6$):δ 1.42 (d, 3H), 5.36 (m, 1H), 5.43 (s, 2H), 6.20 (d, 2H), 6.45 (dlike, 1H), 7.11 (t, 1H), 7.30 (m, 1H), 7.39 (d, 1H), 7.50 (m, 2H), 7.55 (d, 1H), 8.43 (d, 1H), 8.50 (s, 1H), 8.92 (s, 1H)

Example 43

N-[3-[5-[1,3-Dimethyl-2-(3-pyridyl)indolyl]]-2-propinyl]-N-hydroxyurea (Compound 43)

(1) Synthesis of 5-bromo-1,3-dimethyl-2-(3-pyridyl) indole

5-Bromo-3-methyl-2-(3-pyridyl)indole instead of 2-(3-pyridyl)indole in Example 24(1), was used for the same manner to obtain 5-bromo-1,3-dimethyl-2-(3-pyridyl) indole.

(2) Synthesis of 3-[5-[1,3-dimethyl-2-(3-pyridyl) indolyl]]-2-propinol

The product obtained in (1) (16.7 g) was dissolved in a mixture of 1,2-dimethoxyethane (57 ml) and water (57 ml), 10% palladium carbon (1.5 g), triphenylphosphine (2.9 g), copper iodide (1.1 g), and potassium carbonate (19.2 g) were suspended, 2-propin-1-ol (8.2 ml) was added, and the mixture was stirred at 80° C. for 2 days. After the reaction, the mixture was filtered through Celite, then the solvent was evaporated and the residue was purified by silica gel column chromatography to obtain 3-[5-[1,3-dimethyl-2-(3-pyridyl) indolyl]]-2-propinol (4.4 g).

(3) Synthesis of 3-[5-[1,3-dimethyl-2-(3-pyridyl) indolyl]]-2-propinylbromide

The product obtained in (2) (182 mg) was dissolved in methylene chloride and stirred with carbon tetrabromide (261 mg) and triphenylphosphine (258 mg) at room temperature for 30 minutes. After the reaction, a saturated aqueous sodium hydrogen carbonate solution was added at 0° C. and the mixture was extracted with methylene chloride and ethyl acetate. The organic phase was washed with brine and dried over magnesium sulfate, then the solvent was evaporated in vacuo to obtain 3-[5-[1,3-dimethyl-2-(3-pyridyl)indolyl]]-2-propinylbromide (155 mg).

(4) Synthesis of 3-[5-[1,3-dimethyl-2-(3-pyridyl) indolyl]]-2-propinylhydroxylamine The product obtained in (3) (913 mg) was dissolved in N-methyl-2-pyrrolidinone (2.1 ml), 50% hydroxylamine aqueous solution (2.1 ml) was dropwise added at 0° C., and the mixture was stirred for one hour. After the reaction, water then methylene chloride (70 ml) were dropwise added and the mixture stirred, then the mixture was extracted with methylene chloride. The organic phase was washed with brine and dried over magnesium sulfate, then the solvent was evaporated in vacuo to obtain 3-[5-[1,3 -dimethyl-2-(3-pyridyl)indolyl]]-2-propinylhydroxylamine.

(5) Synthesis of N-[3-[5-[1,3-dimethyl-2-(3-pyridyl) indolyl]]-2-propinyl]-N-hydroxyurea The product obtained in (4) was treated in the same way as in Example 1(3) to obtain N-[3-[5-[1,3-dimethyl-2-(3-pyridyl)indolyl]]-2-propinyl]-N-hydroxyurea.

$^{1}$H-NMR (DMSO-d$_6$):δ 2.21 (s, 3H), 3.61 (s, 3H), 4.36 (s, 2H), 6.56 (s, 2H), 7.25 (d, 1H), 7.48 (d, 1H), 7.58 (m, 1H), 7.67 (slike, 1H), 7.93 (dlike, 1H), 8.67 (dlike, 1H), 8.69 (slike, 1H), 9.61 (s, 1H)

Example 44

N-[2-[4-[5-[1,3-dimethyl-2-(3-pyridyl)indolyl]]-3-butynyl]]-N-hydroxyurea (Compound 44)

(1) Synthesis of 4-[5-[1,3-dimethyl-2-(3-pyridyl)indolyl]]-3-butin-2-ol

1-Butin-3-ol instead of 2-propin-1-ol in Example 43(2), was used for the same manner to obtain 4-[5-[1,3-dimethyl-2-(3-pyridyl)indolyl]]-3-butin-2-ol.

(2) Synthesis of N-[2-[4-[5-[1,3-dimethyl-2-(3-pyridyl)indolyl]]-3-butynyl]]-N-hydroxyurea The product obtained in (1) was treated in the same way as in Example 43(3) to (5) to obtain N-[2-[4-[5-[1,3-dimethyl-2-(3-pyridyl)indolyl]]-3-butynyl]]-N-hydroxyurea.

$^{1}$H-NMR (DMSO-d$_6$):δ 1.39 (d, 3H), 2.21 (s, 3H), 3.61 (s, 3H), 5.15 (m, 1H), 6.53 (s, 2H), 7.22 (m, 1H), 7.48 (d, 1H), 7.58 (m, 1H), 7.64 (slike, 1H), 7.94 (dlike, 1H), 8.67 (m, 1H), 8.69 (d, 1H), 9.32 (s, 1H)

Example 45

N-Hydroxy-N-[1-[5-[1-methyl-3-(3-pyridyl)indolyl]]ethyl]urea (Compound 45)

The product obtained in Example 40(2) was treated in the same way as in Example 31(1) to (2) to obtain N-hydroxy-N-[1-[5-[1-methyl-3-(3-pyridyl) indolyl]]ethyl]urea.

$^{1}$H-NMR (DMSO-d$_6$):δ 1.49 (d, 3H), 3.83 (s, 3H), 5.43 (m, 1H), 6.26 (s, 2H), 7.26 (dlike, 1H), 7.44 (d, 1H), 7.46 (m, 1H), 7.79 (s, 1H), 7.83 (slike, 1H), 8.02 (dlike, 1H), 8.43 (dlike, 1H), 8.88 (d, 1H), 9.02 (s, 1H)

Example 46

N-[5-[1,3-Dimethyl-2-(3-pyridyl)indolyl]methyl]-N-hydroxyurea hydrochloride (Compound 46)

The compound 35 (1.35 g) was dissolved in ethanol (100 ml) and recrystallized at 0° C. by 0.1N hydrochloric acid ethanol solution (44 ml) to obtain N-[5-[1,3-dimethyl-2-(3-pyridyl)indolyl]methyl]-N-hydroxyurea hydrochloride (760 mg).

$^{1}$H-NMR (DMSO-d$_6$):δ 2.25 (s, 3H), 3.64 (s, 3H), 4.63 (s, 2H), 7.21 (m, 1H), 7.45 (d, 1H), 7.51 (s, 1H), 7.98–8.55 (m, 1H), 8.44–8.52 (m, 1H), 8.87–8.89 (m, 1H), 8.99 (s, 1H)

The structures of the substituent groups of the compounds obtained in the above Examples are shown in Table 1.

TABLE 1

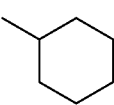

| Ex. | R$_1$ | R$_2$ | R$_3$ | R$_4$ | R$_5$ | R$_6$ | B |
|---|---|---|---|---|---|---|---|
| 1 | A | 3-pyridyl | H | H | H | H | (CH$_2$)$_{11}$ |
| 2 | A | 3-pyridyl | H | H | H | H | (CH$_2$)$_5$ |
| 3 | A | 3-pyridyl | H | H | H | H | CH$_2$ |
| 4 | A | 3-pyridyl | Cl | H | H | H | (CH$_2$)$_5$ |
| 5 | A | 3-pyridyl | H | Cl | H | H | (CH$_2$)$_5$ |
| 6 | A | 3-pyridyl | H | H | H | H | (CH$_2$)$_7$ |
| 7 | A | 3-pyridyl | H | H | H | H | (CH$_2$)$_3$ |
| 8 | A | 3-pyridyl | Cl | H | H | H | (CH$_2$)$_3$ |
| 9 | A | 3-pyridyl | Cl | Cl | H | H | (CH$_2$)$_5$ |
| 10 | A | 3-pyridyl | Me | Cl | H | H | (CH$_2$)$_5$ |
| 11 | A | 3-pyridyl | H | H | H | H | (CH$_2$)$_9$ |
| 12 | A | 3-pyridyl | Me | F | H | H | (CH$_2$)$_5$ |
| 13 | A | 3-pyridyl | Me | H | H | H | (CH$_2$)$_5$ |
| 14 | A | 3-pyridyl | H | H | cyclohexyl | H | (CH$_2$)$_{11}$ |
| 15 | A | 3-pyridyl | Me | F | Me | H | (CH$_2$)$_5$ |
| 16 | A | 3-pyridyl | —(CH$_2$)$_5$—COOH | H | H | H | (CH$_2$)$_5$ |
| 17 | A | H | 3-pyridyl-methyl | H | H | H | CH$_2$ |
| 18 | A | H | 3-pyridyl-methyl | H | H | H | (CH$_2$)$_5$ |

TABLE 1-continued

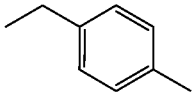

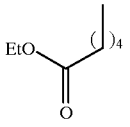

| Ex. | R₁ | R₂ | R₃ | R₄ | R₅ | R₆ | B |
|---|---|---|---|---|---|---|---|
| 19 | A | H | 3-pyridyl | H | H | H | CH₂ |
| 20 | A | Me | 3-pyridyl | H | H | H | CH₂ |
| 21 | A | H | 3-pyridyl | H | H | H | (CH₂)₅ |
| 22 | A | H | 3-pyridyl-methyl | F | H | H | (CH₂)₅ |
| 23 | H | 3-pyridyl | A | H | H | H | Bond |
| 24 | Me | 3-pyridyl | A | H | H | H | Vinylene |
| 25 | 3-pyridyl-methyl | H | A | H | H | H | Vinylene |
| 26 | 3-pyridyl-methyl | H | A | H | H | H | Bond |
| 27 | 3-pyridyl-methyl | H | A | H | H | H | 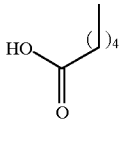 |
| 28 | 3-(3-pyridyl)propyl | H | A | H | H | H | Bond |
| 29 | 3-pyridyl-methyl | H | A | Br | H | H | Bond |
| 30 | 3-pyridyl-methyl | Me | A | H | H | H | Bond |
| 31 | 3-pyridyl-methyl | H | A | H | Me | H | Bond |
| 32 | 3-pyridyl-methyl | H | A | F | H | H | Bond |
| 33 | 3-pyridyl-methyl | H | H | A | H | H | Bond |
| 34 | Me | 3-pyridyl | Me | A | H | H | Vinylene |
| 35 | Me | 3-pyridyl | Me | A | H | H | Bond |
| 36 | EtO(CH₂)₄C(O)– | 3-pyridyl | Me | A | H | H | Bond |
| 37 | HO(CH₂)₄C(O)– | 3-pyridyl | Me | A | H | H | Bond |
| 38 | Me | 3-pyridyl | Me | A | H | H | (CH₂)₂ |
| 39 | 3-(3-pyridyl)propyl | H | H | A | H | H | Bond |
| 40 | Me | H | 3-pyridyl | A | H | H | Bond |
| 41 | Me | 3-pyridyl | Me | A | Me | H | Bond |
| 42 | 3-pyridyl-methyl | H | H | A | Me | H | Bond |
| 43 | Me | 3-pyridyl | Me | A | H | H | Ethynylene |
| 44 | Me | 3-pyridyl | Me | A | Me | H | Ethynylene |
| 45 | Me | H | 3-pyridyl | A | Me | H | Bond |
| 46 | Me | 3-pyridyl | Me | A | H | H | Bond |

Preparation Examples will be shown below:

Example 47

(Preparation of Tablets)

| | |
|---|---|
| Present compound (Compound 1) | 250 g |
| Lactose | 620 g |
| Corn starch | 400 g |
| Hydroxypropyl cellulose | 20 g |
| Magnesium stearate | 10 g |

The above compound of the present invention, lactose, and corn starch were mixed until becoming homogeneous, then a 5 w/v% ethanol solution of hydroxypropyl cellulose was added and the mixture was mixed and granulated. The granules were graded by passing them through a 16 mesh sieve, then were formed into tablets by an ordinary method to form tablets of a weight per tablet of 130 mg, a diameter of 7 mm, and a content of the drug of 25 mg.

Example 48

(Preparation of Capsules)

| | |
|---|---|
| Present compound (Compound 3) | 250 g |
| Lactose | 620 g |
| Abicel | 620 g |
| Magnesium stearate | 10 g |

The compound of the present invention, lactose, abicel, and magnesium stearate were sufficiently mixed until becoming homogeneous, then the mixture was filled into No. 3 capsules to obtain capsules of a weight per capsule of 150 mg and a content of the drug of 25 mg.

Test Examples will be shown below.

Test Example 1

(Test of Thromboxane synthase Inhibitory Activity)

Human platelet microsomes were used and a test performed using as an indicator the amount of production of the thromboxane $A_2$ stable metabolite thromboxane $B_2$. A buffer solution (20 mM tris-HCl buffer solution, 1 mM EDTA, pH 7.5) containing human platelet microsomes (50 μg protein/ml) and the test compound (final concentration of $10^{-6}$M) was stirred, then incubated at 0° C. for 30 minutes, followed by adding prostaglandin $H_2$ (100 ng/2 μl). This was made acidic to stop the reaction, then neutralized with 1M Tris-base, then centrifuged at 3000 rpm for 20 minutes. The amount of the thromboxane $B_2$ in the supernatant was measured by the EIA method (Cayman Co. kit).

As the test compound, the compounds 1, 6, 10, 11, 18 to 21, 24 to 27, 35, 40, 41, 44, and 45 were used for the test. The activity of the compounds in inhibiting production of thromboxane $B_2$ (TxSI) is shown in Table 2 by the $IC_{50}$.

Test Example 2

(Test of Lipoxygenase Inhibitory Activity)

Using rat polymorphonuclear leukocytes, a test was conducted using as an indicator the amount of production of leukotriene $B_4$. Wistar male rats (Japan Clea) were intraperitoneally administered with 12% sodium casein. After 16 hours, the peritoneal cavities were lavaged and the polymorphonuclear leukocytes were recovered. The polymorphonuclear leukocytes thus obtained were suspended in a phosphate buffer (137 mM NaCl, 3 mM KCl, 8 mM $Na_2HPO_4$, 2 mM $KH_2PO_4$) ($2.5 \times 10^5$ cells/0.4 ml), then the test compound (final concentration $10^{-5}$M) was added and incubation performed for 10 minutes at 37° C. then a calcium solution (10 mM $CaCl_2$, 0.86% NaCl) 0.1 ml was added and incubation performed for 5 minutes, then 1.25 μl of calcium ionophore (20 μm, A-23187) was added and the reaction started. Five minutes after the addition, 250 μl of methanol was added to stop the reaction. After the reaction was stopped, the result was centrifuged for 20 minutes (4° C., 3000 rpm), then the amount of leukotriene $B_4$ in the supernatant was measured by the EIA method (Cayman Co. kit).

As the test compound, the same compounds as in Test Example 1 were used for the test. The activity of the compounds in inhibiting the production of leukotriene $B_4$ (LTBI) is shown in Table 2 by the $IC_{50}$.

TABLE 2

| Compound no. | TxSI $IC_{50}$ (μM) | LTBI $IC_{50}$ (μM) |
|---|---|---|
| 1 | 0.003 | 0.006 |
| 6 | 0.0007 | 0.01 |
| 10 | 0.0007 | 0.03 |
| 11 | 0.0008 | 0.009 |
| 18 | 0.3 | 0.1 |
| 19 | 0.015 | 0.3 |
| 20 | 0.005 | 1.5 |
| 21 | 0.015 | 0.04 |
| 24 | 0.04 | 4.0 |
| 25 | 0.15 | 0.2 |
| 26 | 0.7 | 3.0 |
| 27 | 0.07 | 0.1 |
| 35 | 0.04 | 2.0 |
| 40 | 0.03 | 0.7 |
| 41 | 0.07 | 2.0 |
| 44 | 0.03 | 0.6 |
| 45 | 0.06 | 2.5 |

Test Example 3

(Measurement of Thromboxane synthase Inhibitory Activity and 5-Lipoxygenase Inhibitory Activity of Rats in Ex Vivo)

For the test animals, SD type male rats were used. These were made to fast from the day before the test. The test drug was suspended in 0.5% sodium carboxymethylcellulose and orally administered one hour before the blood was taken. The blood was taken from the abdominal aorta and divided for the measurement of the thromboxane synthase inhibitory activity and the 5-lipoxygenase inhibitory activity.

The thromboxane synthase activity was shown using as an indicator the amount of production of the thromboxane $A_2$ stable metabolite thromboxane $B_2$. The divided blood was allowed to naturally coagulate (25° C., 90 minutes) and then the serum was centrifuged (3000 rpm, 20 minutes, 4° C.) and the amount of thromboxane $B_2$ in the serum was measured by the EIA method. For the thromboxane synthase inhibitory activity, the 50% inhibitory amount was calculated from the rate of inhibition of the test drug group with respect to the solvent control group.

The 5-lipoxygenase activity was shown using as an indicator the amount of production of leukotriene $B_4$. 50 pM calcium ionophor (A23187) was added to the divided blood to start the reaction (37° C., 30 minutes), and 1 mM Indomethacin, 1 mM Phenidone, and 0.1 mM EGTA were added to stop the reaction. The plasma was centrifuged (3000 rpm, 20 minutes, 4° C.) and the leukotriene $B_4$ in the plasma was measured by the EIA method. For the 5-lipoxygenase inhibitory activity, the 50% inhibitory amount was calculated from the rate of inhibition of the test drug group with respect to the solvent control group.

As the test compounds, the above compounds 18 to 21, 24 to 26, 31, 33, 35, 40, 41 and 45 were used for the test. The results are shown in Table 3.

TABLE 3

| Compound no. | $ED_{50}$ (/kg) | |
| --- | --- | --- |
| | TxSI | LTBI |
| 18 | 20 | 14 |
| 19 | 3 | 3 |
| 20 | 1.5 | 17 |
| 21 | 1.0 | 28 |
| 24 | 30 | 13 |
| 25 | 30 | 5 |
| 26 | 25 | 9 |
| 31 | 20 | 19 |
| 33 | 6 | 10 |
| 35 | 12 | 8.5 |
| 40 | 7 | 5 |
| 41 | 1.0 | 15 |
| 45 | 13 | 20 |

Test Example 4

(Pharmacological Activity on Antigen-Induced Bronchoconstriction Model of Guinea Pig)

Guinea pigs sensitized by ovalbumin were used and orally administered with the test compound suspended in 5% gum arabic. The activity for inhibiting antigen-induced bronchoconstriction after one hour after administration was measured by the Konzett-Rossler method.

Each of the sensitized guinea pigs was anesthesized by 35 mg/kg pentobarbital, a cannula was inserted into the respiratory tract and connected to an artificial respirator, a cannula was inserted into the jugular vein, and treatment was performed by 5 mg/kg suxamethonium and 5 g/kg mepyramine. Next, the guinea pig was inhaled a nebulized ovalbumin to cause bronchoconstriction and the activity in inhibiting bronchoconstriction was found from the ratio of the amount of overflow volume to the detector to the amount of air blown volume from the artificial respirator.

As the test compound, the Compounds 19, 26, and 33 were used. As the control, the thromboxane synthase inhibitor OKY-046 and the 5-lipoxygenase inhibitor A-64077 were used. The results are shown in Table 4:

TABLE 4

| Compound no. | Suppression of respiratory constriction ($ED_{50}$: mg/kg) |
| --- | --- |
| 19 | 30 |
| 26 | 75 |
| 33 | 30 |
| OKY-046 | 260 |
| A-64077 | 300 |

From the results of the Test Examples 1 to 3, it is learned that the present compounds have the two activities of a lipoxygenase inhibitory activity and a thromboxane synthase inhibitory activity. Further, from Test Example 4, it is learned that since an effect of inhibition of bronchoconstriction is exhibited in an antigen-induced respiratory constriction model of guinea pigs, the compounds are useful as drugs for the treatment of asthma.

Test Example 5

(Acute Toxicity Test)

Crj-ICR male mice (7 weeks old, five mice to a group) were used. The test compound (Compounds 9, 26, and 33) was suspended in 0.5% sodium carboxymethylcellulose and administered intraperitoneally at a ratio of 10 ml/kg. The survival of the animals was observed up until 7 days after administration.

As a result, no deaths were observed at dosages of up to 1000 mg/kg.

INDUSTRIAL APPLICABILITY

The compounds of the present invention have a strong inhibitory activity against lipoxygenase and thromboxane synthase, and therefore, are useful as a drug for treatment of allergic diseases or inflammatory diseases, more specifically, as a drug for the treatment or prevention of various diseases arising from the metabolites of arachidonic acid, for example, asthma, psoriasis, enteritis, nephritis, ischemia.

What is claimed is:

1. An N-hydroxyurea derivative having the formula (IL:

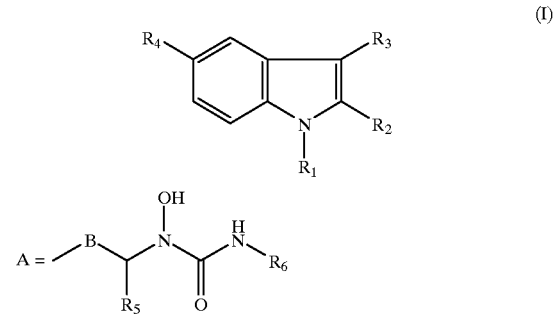

wherein, in the formula (I), $R_1$ represents A, either one of $R_2$, $R_3$, and $R_4$ represents a 3-pyridyl group or 3-pyridyl lower alkyl group, the remaining groups of $R_2$, $R_3$, and $R_4$, independently represent a hydrogen atom, a halogen atom, or a substituted or unsubstituted $C_1$ to $C_5$ alkyl group, where the substituent represents a carboxyl group, a methoxycarbonyl group, or an ethoxycarbonyl group, $R_5$ represents a hydrogen atom, a methyl group, or an ethyl group, $R_6$ represents a hydrogen atom, a methyl group, an ethyl group, or a $C_3$ to $C_6$ cycloalkyl group, and B represents a bond or a $C_1$ to $C_{12}$ linear alkylene group.

2. An N-hydroxyurea derivative having the formula (I):

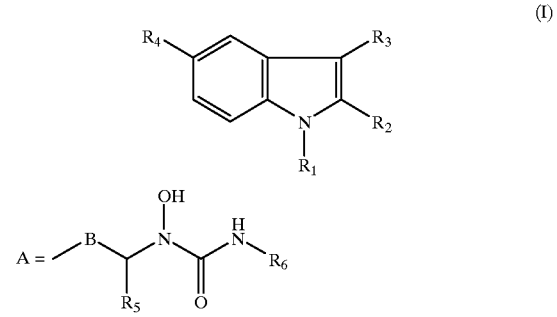

herein in the formula (I), $R_3$ represents A, either one of $R_1$, $R_2$, and $R_4$ represents a 3-pyridyl group or 3-pyridyl lower alkyl group, the remaining groups of $R_1$, $R_2$ and $R_4$ independently represent a hydrogen atom, a halogen atom, or a substituted or unsubstituted $C_1$ to $C_5$ alkyl group, where the substituent represents a carboxyl group, a methoxycarbonyl group, or an ethoxycarbonyl group, $R_5$ represents a hydrogen atom, a methyl group, or an ethyl group, $R_6$ represents a hydrogen atom, a methyl grout, an ethyl group, or $C_3$ to $C_6$ cycloalkyl group, and B represents a bond, a $C_1$ to $C_5$ alkylene group, or a $C_2$ and $C_5$ alkenylene group, or B—C ($R_5$) represents a $C_2$ to $C_4$ alkylene group having a benzene ring in the middle thereof.

3. An N-hydroxyurea derivative having the formula (I):

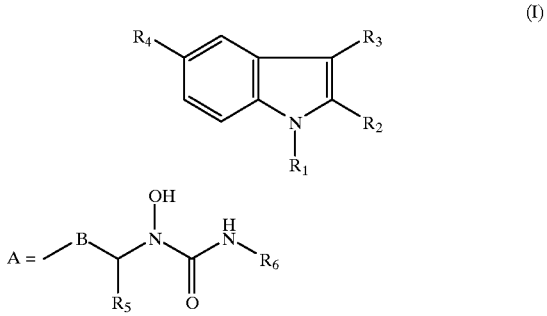

(I)

wherein in the formula (I), $R_4$ represents A, either one of $R_1$, $R_2$, and $R_3$ represents a 3-pyridyl group or 3-pyridyl lower alkyl group, the remaining groups of $R_1$, $R_2$, and $R_3$ independently represent a hydrogen atom, a halogen atom, or a substituted or unsubstituted $C_1$ to $C_5$ alkyl group, where the substituent represents a carboxyl group, a methoxycarbonyl group, or an ethoxycarbonyl group, $R_5$ represents a hydrogen atom, a methyl group, or an ethyl group, $R_6$ represents a hydrogen atom, a methyl group, an ethyl group, or $C_3$ to $C_5$ cycloalkyl group, and B represents a bond, a $C_1$ to $C_5$ alkylene group, a $C_2$ to $C_5$ alkenylene group, or a $C_2$ to $C_5$ alkynylene group.

4. An N-hydroxyurea derivative as claimed in claim 1, wherein, in the formula (I), $R_1$ represents A, $R_2$ represents a 3-pyridyl group, $R_3$ and $R_4$ independently represent a hydrogen atom, halogen atom, methyl group, or carboxypentyl group, $R_5$ represents a hydrogen atom or methyl group, $R_6$ represents a hydrogen atom or cyclohexyl group, and B represents a $C_1$ to $C_{12}$ linear alkylene group.

5. An N-hydroxyurea derivative as claimed in claim 2, wherein, in the formula (I), $R_3$ represents A, $R_1$ represents a 3-pyridylmethyl group or 3-pyridylpropyl group, $R_2$ and $R_4$ independently represent a hydrogen atom, halogen atom, or methyl group, $R_5$ represents a hydrogen atom or methyl group, $R_6$ represents a hydrogen atom, B represents a bond or vinylene group or B—C($R_5$) represents a $C_1$ to $C_4$ alkylene group having a benzene ring in the middle thereof.

6. An N-hydroxyurea derivative as claimed in claim 3, wherein, in the formula (I), $R_4$ represents A, $R_1$ represents a 3-pyridylmethyl group or 3-pyridylpropyl group, $R_2$ and $R_3$ independently represent a hydrogen atom or methyl group, $R_5$ represents a hydrogen atom or methyl group, $R_6$ represents a hydrogen atom, and B represents a bond.

7. An N-hydroxyurea derivative as claimed in claim 3, wherein, in the formula (I), $R_4$ represents A, $R_2$ represents a 3-pyridyl group, $R_1$ and $R_3$ independently represent a hydrogen atom, methyl group, carboxybutyl group, or ethoxycarbonylbutyl group, $R_5$ represents a hydrogen atom or methyl group, $R_6$ represents a hydrogen atom, and B represents a bond, ethylene group, vinylene group, or ethynylene group.

8. An N-hydroxyurea derivative as claimed in claim 4, wherein, in the formula (I), $R_3$ represents a hydrogen atom, chlorine atom, methyl group, or carboxypentyl group and $R_4$ represents a hydrogen atom, fluorine atom, or chlorine atom.

9. An N-hydroxyurea derivative as claimed in claim 1, wherein, in the formula (I), $R_1$ represents A, $R_3$ represents a 3-pyridyl group or 3-pyridylmethyl group, $R_2$ and $R_4$ independently represent a hydrogen atom, halogen atom, or methyl group, $R_5$ represents a hydrogen atom or methyl group, $R_6$ represents a hydrogen atom, and B represents a $C_1$ to $C_6$ linear alkylene group.

10. An N-hydroxyurea derivative as claimed in claim 2, wherein, in the formula (I), $R_3$ represents A, $R_2$ represents a 3-pyridyl group, $R_1$ and $R_4$ independently represent a hydrogen atom or methyl group, $R_5$ represents a hydrogen atom or methyl group, $R_6$ represents a hydrogen atom, and B represents a bond or vinylene group.

11. An N-hydroxyurea derivative as claimed in claim 5, wherein, in the formula (I), $R_1$ represents a 3-pyridylmethyl group, $R_2$ and $R_4$ independently represent a hydrogen atom, fluorine atom, bromine atom, or methyl group, and B represents a bond or vinylene group.

12. An N-hydroxyurea derivative as claimed in claim 6, wherein, in the formula (I), $R_1$ represents a 3-pyridylmethyl group, $R_2$ and $R_3$ represent a hydrogen atom, and B represents a bond.

13. An N-hydroxyurea derivative as claimed in claim 7, wherein, in the formula (I), $R_1$ represents a methyl group, carboxybutyl group, or ethoxycarbonylbutyl group, $R_3$ represents a methyl group, and B represents a bond, ethylene group, vinylene group, or ethynylene group.

14. An N-hydroxyurea derivative as claimed in claim 3, wherein, in the formula (I), $R_4$ represents A, $R_3$ represents a 3-pyridyl group, $R_1$ and $R_2$ independently represent a hydrogen atom or methyl group, and B represents a bond.

15. A pharmaceutical composition comprising an N-hydroxyurea derivative according to any one of claims 1 to 14 or its pharmacologically acceptable salt or the hydrate or solvate thereof and a carrier.

16. An antiallergic or anti-inflammatory drug comprising an N-hydroxyurea derivative according to any one of claims 1 to 14 or its pharmacologically acceptable salt or the hydrate or solvate thereof, as an effective ingredient.

* * * * *

UNITED STATES PATENT AND TRADEMARK OFFICE
CERTIFICATE OF CORRECTION

PATENT NO.   : 6,184,238 B1
DATED        : February 6, 2001
INVENTOR(S)  : Michika Takano, Toshiya Komatsu and Yoshikazu Kawahara It is certified that error appears in the above-identified patent and that said Letters Patent is hereby corrected as shown below:

<u>Column 34,</u>
Line 22, replace "formula (IL:" with -- formula (I): --.

<u>Column 35,</u>
Line 5, replace "methyl grout" with -- methyl group --.
Lines 33-34, replace "or $C_3$ to $C_5$ cycloalkyl group" with -- or $C_3$ to $C_6$ cycloalkyl group --

Signed and Sealed this

Twenty-eighth Day of May, 2002

*Attest:*

*Attesting Officer*

JAMES E. ROGAN
*Director of the United States Patent and Trademark Office*